US011915798B2

(12) United States Patent
Jippo

(10) Patent No.: US 11,915,798 B2
(45) Date of Patent: Feb. 27, 2024

(54) MATERIAL CHARACTERISTIC PREDICTION APPARATUS AND MATERIAL CHARACTERISTIC PREDICTION METHOD

(71) Applicant: FUJITSU LIMITED, Kawasaki (JP)

(72) Inventor: Hideyuki Jippo, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 898 days.

(21) Appl. No.: 16/886,307

(22) Filed: May 28, 2020

(65) Prior Publication Data

US 2020/0381085 A1 Dec. 3, 2020

(30) Foreign Application Priority Data

May 30, 2019 (JP) ................................ 2019-101217

(51) Int. Cl.

| | |
|---|---|
| ***G16C 20/30*** | (2019.01) |
| ***G06N 3/12*** | (2023.01) |
| ***G06N 3/126*** | (2023.01) |
| ***G06N 5/022*** | (2023.01) |
| ***G06N 5/04*** | (2023.01) |
| ***G06N 5/048*** | (2023.01) |
| ***G06N 20/00*** | (2019.01) |
| ***G06N 20/10*** | (2019.01) |
| ***G16C 20/40*** | (2019.01) |
| ***G16C 20/70*** | (2019.01) |

(52) U.S. Cl.

CPC ............ *G16C 20/30* (2019.02); *G06N 3/126* (2013.01); *G06N 5/048* (2013.01); *G16C 20/70* (2019.02); *G06N 3/12* (2013.01); *G06N 5/022* (2013.01); *G06N 5/04* (2013.01); *G06N 20/00* (2019.01); *G06N 20/10* (2019.01); *G16C 20/40* (2019.02)

(58) Field of Classification Search

CPC ........ G16C 20/30; G16C 20/70; G16C 20/40; G06N 3/126; G06N 5/048; G06N 5/022; G06N 20/00; G06N 20/10; G06N 5/04; G06N 3/12

See application file for complete search history.

(56) References Cited

U.S. PATENT DOCUMENTS

| | | | | |
|---|---|---|---|---|
| 2005/0004900 | A1 | 1/2005 | Hisamitsu et al. | |
| 2020/0349451 | A1* | 11/2020 | Suzuki .................. | G01N 33/00 |

FOREIGN PATENT DOCUMENTS

| | | |
|---|---|---|
| JP | 2004-295654 A | 10/2004 |
| JP | 2004-334753 A | 11/2004 |

OTHER PUBLICATIONS

Knisley et al. (Graph Theoretic Models in Chemistry and Molecular Biology. In Handbook of Applied Algorithms (eds A. Nayak and I. Stojmenović 2008) (Year: 2008).*

(Continued)

*Primary Examiner* — Manish S Shah
*Assistant Examiner* — Christian T Bryant
(74) *Attorney, Agent, or Firm* — Fujitsu Patent Center

(57) ABSTRACT

An apparatus includes a memory and a processor coupled to the memory. The processor is configured to: determine a degree of similarity between a target material and a first material based on a structure and characteristic of each of the target material and the first material; predict a characteristic value of the target material based on a first value representing the characteristic of the first material; and output the predicted characteristic value.

12 Claims, 30 Drawing Sheets

MOLECULE A: ACETIC ACID

MOLECULE B: METHYL ACETATE

(56) References Cited

OTHER PUBLICATIONS

Maritza Hernandez al., "A Novel Graph-based Approach for Determining Molecular Similarity", 2016 1QB Information Technologies (1QBit), arXiv:1601.06693v1, pp. 1-15, Jan. 25, 2016, Internet: https://arxiv.org/pdf/1601.06693.pdf (Total 16 pages).
Nino Shervashidze et al., "Weisfeiler-Lehman Graph Kernels", Journal of Machine Learning Research 12, pp. 2539-2561, Sep. 2011 (Total 23 pages).

* cited by examiner

MOLECULE A:
ACETIC ACID

MOLECULE B:
METHYL ACETATE

SIZE: 3

SIZE: 4

10

[0] CID6582 (191.3)

[3] CID31374 (37.78)

ONE EMBODIMENT

[0] CID6582 (191.3)

[3] CID31254 (182.4)

RELATED ART

ONE EMBODIMENT

| | N-METHYLACETAMIDE RELATIVE PERMITTIVITY : 191.3 (QUERY MATERIAL) | N-METHYLFORMAMIDE RELATIVE PERMITTIVITY : 182.4 | N,N-DIMETHYLACETAMIDE RELATIVE PERMITTIVITY : 37.78 |
|---|---|---|---|
| LABEL IN RELATED ART |  |  |  |
| DEGREE OF SIMILARITY CALCULATED ONLY FROM STRUCTURE | 1 | 0.7777 | 0.825 |
| WL LABEL IN ONE EMBODIMENT |  |  |  |
| DEGREE OF SIMILARITY ACCORDING TO CHARACTERISTIC | 1 | 0.8 | 0.6 |

FIG. 26B

| | | |
|---|---|---|
| RELATIVE PERMITTIVITY | N-METHYLACETAMIDE > N-METHYLFORMAMIDE > N-IMETHYLACETAMIDE | |
| DEGREE OF SIMILARITY CALCULATED ONLY FROM STRUCTURE | N-METHYLACETAMIDE > N,N-IMETHYLACETAMIDE > N-METHYLFORMAMIDE | RESPECTIVE ORDERS OF RELATIVE PERMITTIVITIES AND DEGREES OF SIMILARITY DO NOT CORRESPOND TO EACH OTHER |
| DEGREE OF SIMILARITY ACCORDING TO CHARACTERISTIC | N-METHYLACETAMIDE > N-METHYLFORMAMIDE > N,N-IMETHYLACETAMIDE | RESPECTIVE ORDERS OF RELATIVE PERMITTIVITIES AND DEGREES OF SIMILARITY CORRESPOND TO EACH OTHER |

PREDICTION ACCURACY OF CHARACTERISTIC VALUE IS HIGH

MATERIAL CHARACTERISTIC PREDICTION APPARATUS AND MATERIAL CHARACTERISTIC PREDICTION METHOD

CROSS-REFERENCE TO RELATED APPLICATION

This application is based upon and claims the benefit of priority of the prior Japanese Patent Application No. 2019401217, filed on May 30, 2019, the entire contents of which are incorporated herein by reference.

FIELD

The embodiments discussed herein are related to a characteristic prediction apparatus and a characteristic prediction method.

BACKGROUND

Generally, compounds (molecules) with similar structure are expected to have similar characteristics (properties). The similar property principle of "similar compounds have similar properties" is widely used when properties of a compound are predicted and the compound having predetermined properties is designed, or when a database of compounds is screened and a compound having predetermined properties is searched for.

Using the similar property principle, for example, it is possible to predict a similar compound found using an existing compound as a query compound, from a database (a compound similar in structure to the query compound) has similar functions (characteristics, physical properties) to those of the query compound. When a new compound is used as a query compound, by searching the database for a compound similar in structure to that of the query compound, it is also possible to predict a characteristic value of a new chemical substance.

Search for compounds similar in structure may be performed by, for example, evaluating a degree of similarity in structure between compounds, and specifying compounds having a high degree of similarity in structure as similar compounds.

As a method for evaluating a degree of similarity in structure between compounds, various methods have been proposed, and for example, a fingerprinting method is widely used. In the fingerprinting method, for example, whether or not a partial structure in a query compound is included in a compound to be compared is represented as 0 or 1, to evaluate a degree of similarity.

As a method for evaluating a degree of similarity in structure, a method is also proposed in which search for a partial structure common to compounds is performed by expressing a maximum independent set problem of a conflict graph by a formula of an Ising model and solving the problem by an annealing machine or the like (see, for example, Maritza Hernandez, Arman Zaribafiyan, Maliheh Aramon, Mohammad Naghibi, "A Novel Graph-based Approach for Determining Molecular Similarity", arXiv: 1601.06693v1 (website: https://arxiv.org/pdf/1601.06693.pdf), referred to as Non-Patent Document 1 hereinafter).

A technique is also known in which, when structure of a compound is graphed and handled, or the like, a label is added to each vertex (corresponding to each atom in a compound) of a graph in consideration of information on coupling vertices (for example, information on bonding atoms) (see, for example, Shervashidze Nino, Schweitzer Pascal, Jan van Leeuwen Erik, Mehlhorn Kurt, Borgwardt Karsten M., "Weisfeiler-Lehman Graph Kernels", Journal of Machine Learning Research, Pp. 2539-2561, 2011).

SUMMARY

According to an aspect of the embodiments, an apparatus includes a memory and a processor coupled to the memory. The processor is configured to: determine a degree of similarity between a target material and a first material based on a structure and characteristic of each of the target material and the first material; predict a characteristic value of the target material based on a first value representing the characteristic of the first material; and output the predicted characteristic value.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 26A and 26B are set of diagrams illustrating an example of a relationship between degree of similarity and characteristic value, in each of one embodiment of the technique disclosed herein and the related art.

DESCRIPTION OF EMBODIMENTS

In the related art, since a characteristic value of a query compound (target material) is predicted based only on information on structure of a compound, prediction accuracy may deteriorate depending on a characteristic to be predicted. In the related art, there was a problem that since it is not possible to calculate a degree of similarity between compounds for each characteristic to be predicted, and it is not possible to search for a similar compound, by focusing on a desired characteristic.

Material Characteristic Prediction Apparatus

A material characteristic prediction apparatus disclosed herein is an apparatus for predicting a characteristic value of a characteristic of a target material. A material characteristic prediction apparatus is an apparatus that predicts a characteristic of a material. The material characteristic prediction apparatus disclosed herein includes a characteristic prediction unit, and further includes other units (including means) as appropriate.

Before describing details of the technique disclosed herein, a method for calculating a degree of similarity between materials in the related art will be described. As one example of the method for calculating a degree of similarity between materials in the related art, a method will be described, in which, by solving a maximum independent set problem of a conflict graph, a partial structure that is common to materials to be compared is searched for, and a degree of similarity is calculated.

When a degree of similarity in structure between compounds is calculated by solving a maximum independent set problem of a conflict graph, the compounds are graphed and handled. Graphing of a compound means, for example, representing structure of the compound, by using information on a type (element) of atom in the compound, and information on bonding state of each atom.

The structure of a compound may be represented by, for example, expression in an MOL format or a structure data file (SDF) format. Usually, the SDI format means a format in which multiple pieces of structural information on compounds expressed in the MOL format are integrated into a single file. In the SDF format file, in addition to the structural information in the MOL format, additional information (for example, catalog number, chemical abstracts service (CAS) number, molecular weight, or the like) for each compound may be handled. Structure of each compound may be graphed, for example, in a comma-separated value (CSV) format in which "atom 1 (name), atom 2 (name), information on an element of the atom 1, information on an element of the atom 2, and a bond order between the atom 1 and the atom 2" are represented as one row.

In the following, a description will be given for a method of creating a conflict graph, using a case as an example where a conflict graph for acetic acid ($CH_3COOH$) and methyl acetate ($CH_3COOCH_3$) is created.

Figure 1:
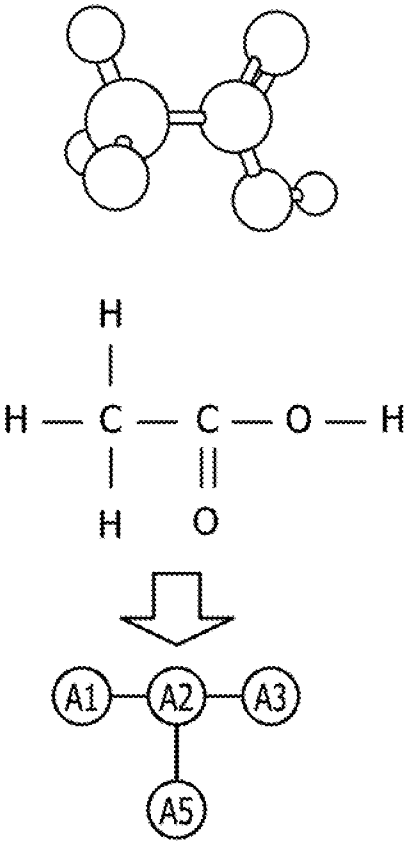
FIG. 1 is a diagram illustrating an example of a state of graphing for making a conflict graph of acetic acid and methyl acetate.
Figure 1:
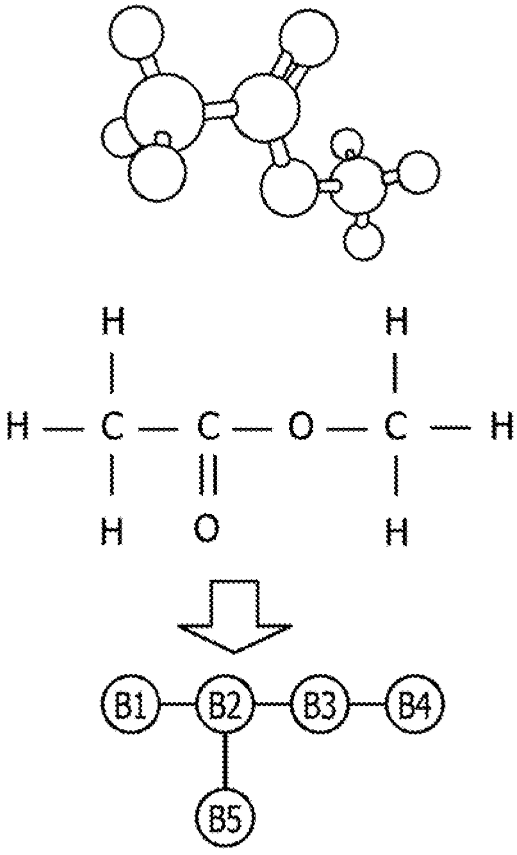

First, graphing acetic acid (hereinafter sometimes referred to as a "molecule A") and methyl acetate (hereinafter sometimes referred to as a "molecule B") results in FIG. 1. In FIG. 1, atoms forming acetic acid are represented by A1, A2, A3, and A5, and atoms forming methyl acetate are represented by B1 to B5. In FIG. 1, A1, A2, B1, B2, and B4 each represent carbon, A3, A5, B3, and B5 each represent oxygen, and a single bond is indicated by a thin solid line, and a double bond is indicated by a thick solid line. In the example illustrated in FIG. 1, atoms other than hydrogen are selected and graphed, but when a compound is graphed, all atoms including hydrogen may be selected and graphed.

Figure 2:
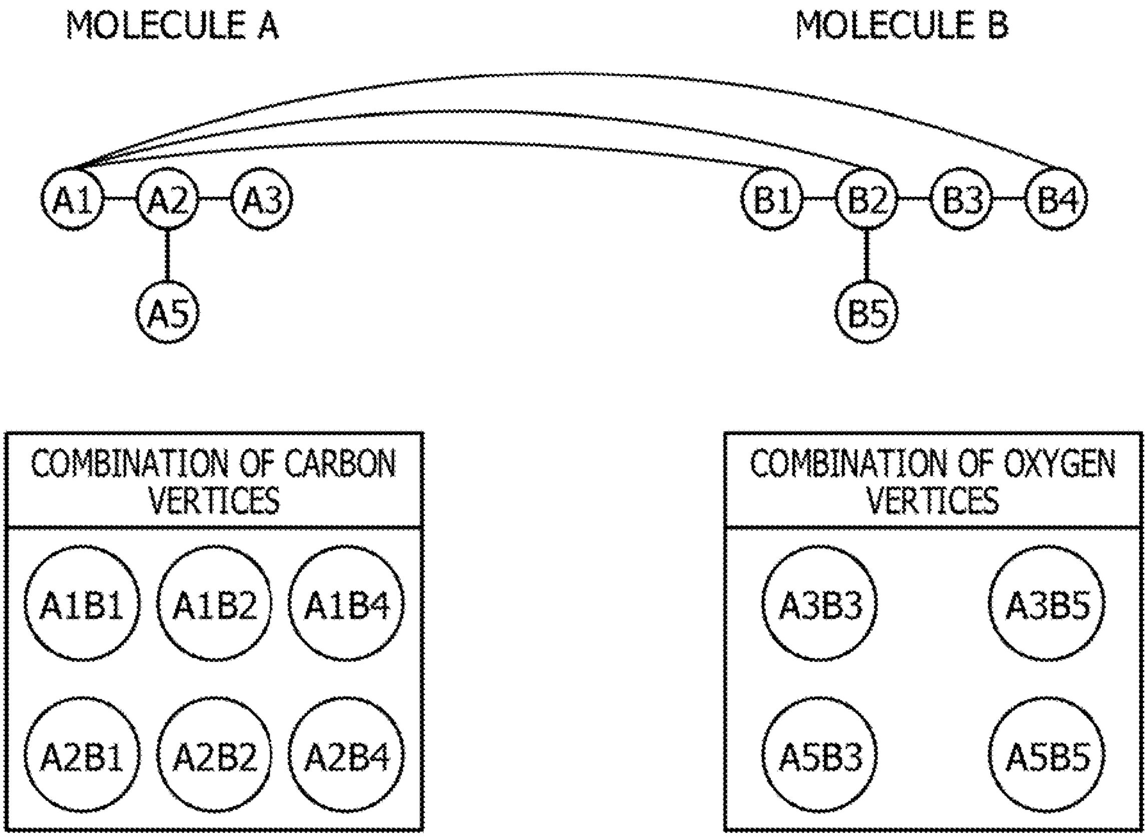
FIG. 2 is a diagram illustrating an example of combination when the same elements in molecules A and B are combined to form nodes of the conflict graph.

Next, vertices (atoms) in the graphed molecules A and B are combined to create vertices (nodes) of the conflict graph. At this time, for example, as illustrated in FIG. 2, it is preferable to combine the same elements in the molecules A and B to form the nodes of the conflict graph. In an example illustrated in FIG. 2, combinations between A1, A2, B1, B2, and B4 representing carbon, and combinations between A3, A5, B3, and B5 representing oxygen are used as nodes of the conflict graph. In this way, by using the combination of the same elements as the node, it is possible to create a conflict graph with a node that may be included in a maximum independent set, thereby reducing the number of nodes and reducing the number of bits of a calculator demanded to solve a maximum independent set problem.

In the example illustrated in FIG. 2, since six nodes are created by combining carbon of the molecule A and carbon of the molecule B, and four nodes are created by combining oxygen of the molecule A and oxygen of the molecule B, the number of nodes in the conflict graph created from the graphed molecules A and B is ten.

Subsequently, edges (branches, sides) in the conflict graph are created. At this time, when two nodes are compared to each other, and the nodes are composed of atoms in different states (for example, atomic number, presence/absence of bonding, bond order, or the like), an edge is created between the two nodes. On the other hand, when two nodes are compared to each other, and the nodes are composed of atoms in the same state, no edge is created between the two nodes.

A rule for creating an edge in the conflict graph will be described with reference to FIG. 3.

First, in the example illustrated in FIG. 3, whether or not to create an edge between a node [A1B1] and a node [A2B2] will be described. As may be seen from structure of the graphed molecule A in FIG. 3, carbon A1 of the molecule A included in the node [A1B1], and carbon A2 of the molecule A included in the node [A2B2] are bonded (single bond) to each other. Similarly, carbon B1 of the molecule B included in the node [A1B1] and carbon B2 of the molecule B included in the node [A2B2] are bonded (single bond) to each other. For example, a state of bonding between the carbon A1 and the carbon A2 and a state of bonding between the carbon B1 and the carbon B2 are identical to each other.

Figure 3:
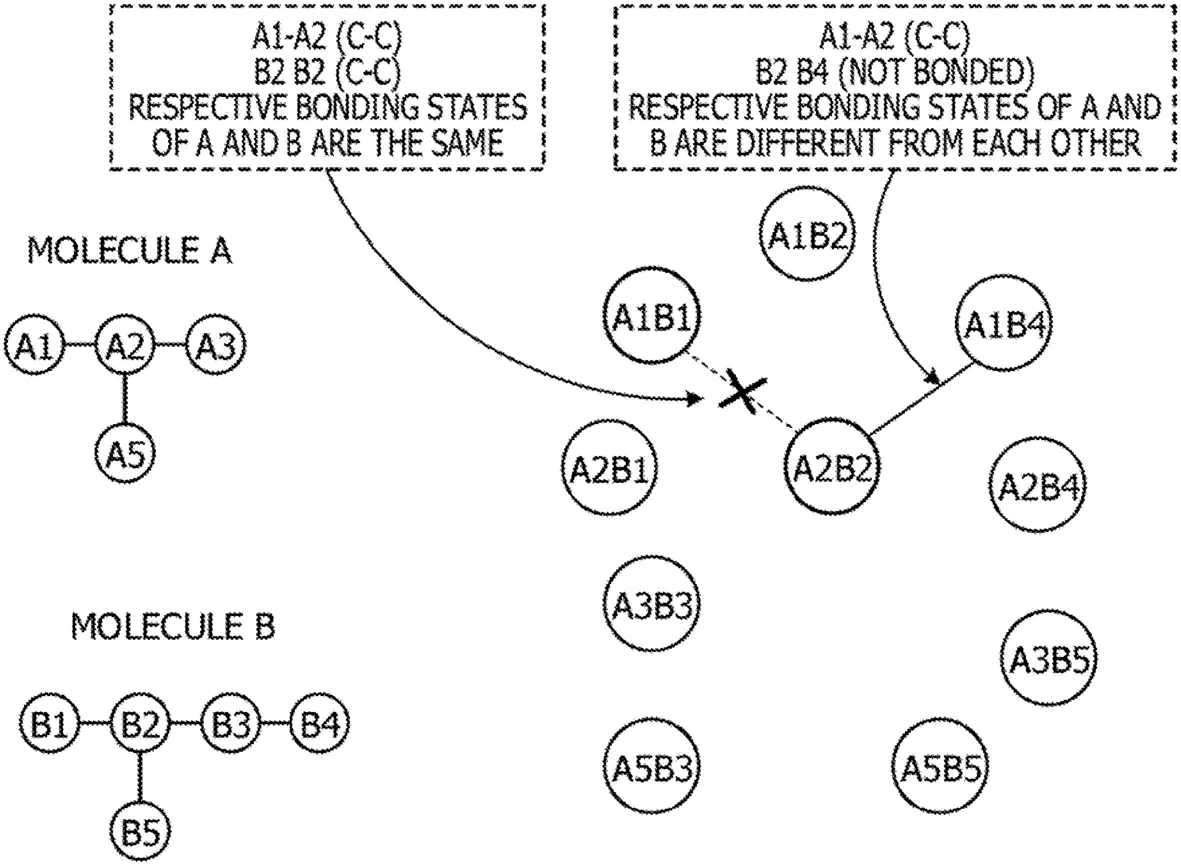
FIG. 3 is a diagram illustrating an example of a rule for edge creation in the conflict graph.

In this way, in the example illustrated in FIG. 3, the state of carbon A1 and carbon A2 in the molecule A and the state of carbon B1 and carbon B2 in the molecule B are identical to each other, and the nodes [A1B1] and the node [A2B2] are nodes that include atoms in the same state. Thus, in the example illustrated in FIG. 3, no edge is created between the node [A1B1] and the node [A2B2].

Next, in the example illustrated in FIG. 3, whether or not to create an edge between a node [A1B4] and the node [A2B2] will be described. As may be seen from the structure of the graphed molecule A in FIG. 3, the carbon A1 of the molecule A included in the node [A1B4] and the carbon A2 of the molecule A included in the node [A2B2] are bonded (single bond) to each other. On the other hand, as may be seen from structure of the graphed molecule B, carbon B4 of the molecule B included in the node [A1B4] and the carbon B2 of the molecule B included in the node [A2B2] sandwich the oxygen B3 therebetween, and are not directly bonded to each other. For example, the state of bonding of the carbon A1 and the carbon A2 and a state of bonding of the carbon B4 and the carbon B2 are different from each other.

For example, in the example illustrated in FIG. 3, the states of carbon A1 and carbon A2 in the molecule A, and the states of carbon B4 and carbon B2 in the molecule B are different from each other, and the node [A1B4] and the node [A2B2] are nodes that include atoms in the different states from each other. For this reason, in the example illustrated in FIG. 3, an edge is created between the node [A1B4] and the node [A2B2].

In this way, it is possible to create the conflict graph based on a rule that, when nodes include atoms in different states from each other, an edge is created between the nodes, and when nodes include atoms in the same state, no edge is created between the nodes.

Figure 4:
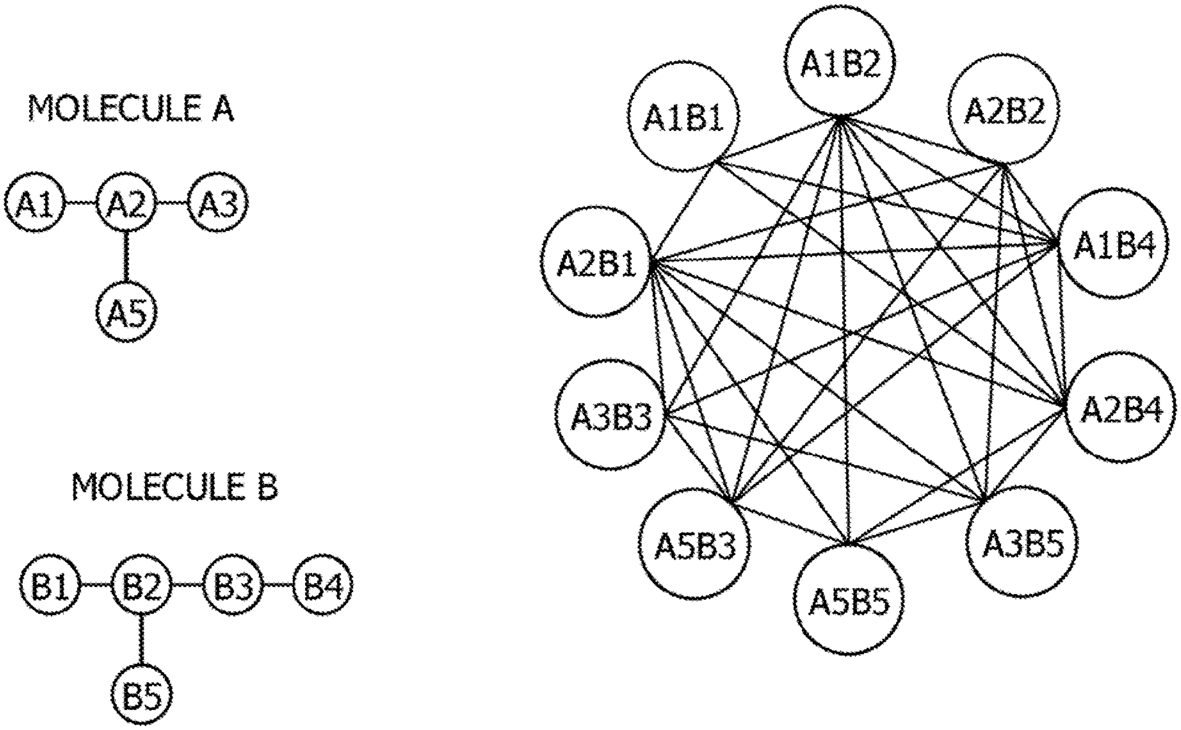
FIG. 4 is a diagram illustrating an example of the conflict graph for the molecule A and the molecule B.

FIG. 4 is a diagram illustrating one example of the conflict graph for the molecule A and the molecule B. As illustrated in FIG. 4, for example, in the node [A2B2] and a node [A5B5], a bonding state of the carbon A2 and oxygen A5 in the molecule A, and a bonding state of the carbon B2 and carbon B5 in the molecule B are identical to each other. Thus, the node [A2B2] and the node [A5B5] are nodes including atoms mutually in the same state, so that no edge is created between the node [A2B2] and the node [A5B5].

It is possible to create an edge of the conflict graph based on, for example, chemical structure data of two compounds for which a degree of similarity in structure is calculated. For example, when chemical structure data of a compound is inputted using an SDF format file, based on information included in the SDF format file, by using a calculator such as a computer for calculation, it is possible to create (specify) an edge of the conflict graph.

Next, a method of solving a maximum independent set problem of a created conflict graph, in one example of the related art described in Non-Patent Document 1 will be described.

A maximum independent set (MIS) in a conflict graph means a set including a largest number of nodes each including no edge therein, among sets of nodes constituting the conflict graph. For example, the maximum independent set in the conflict graph means a set having a largest size (the number of nodes) among sets each formed by nodes each including no edge therein.

Figure 5:
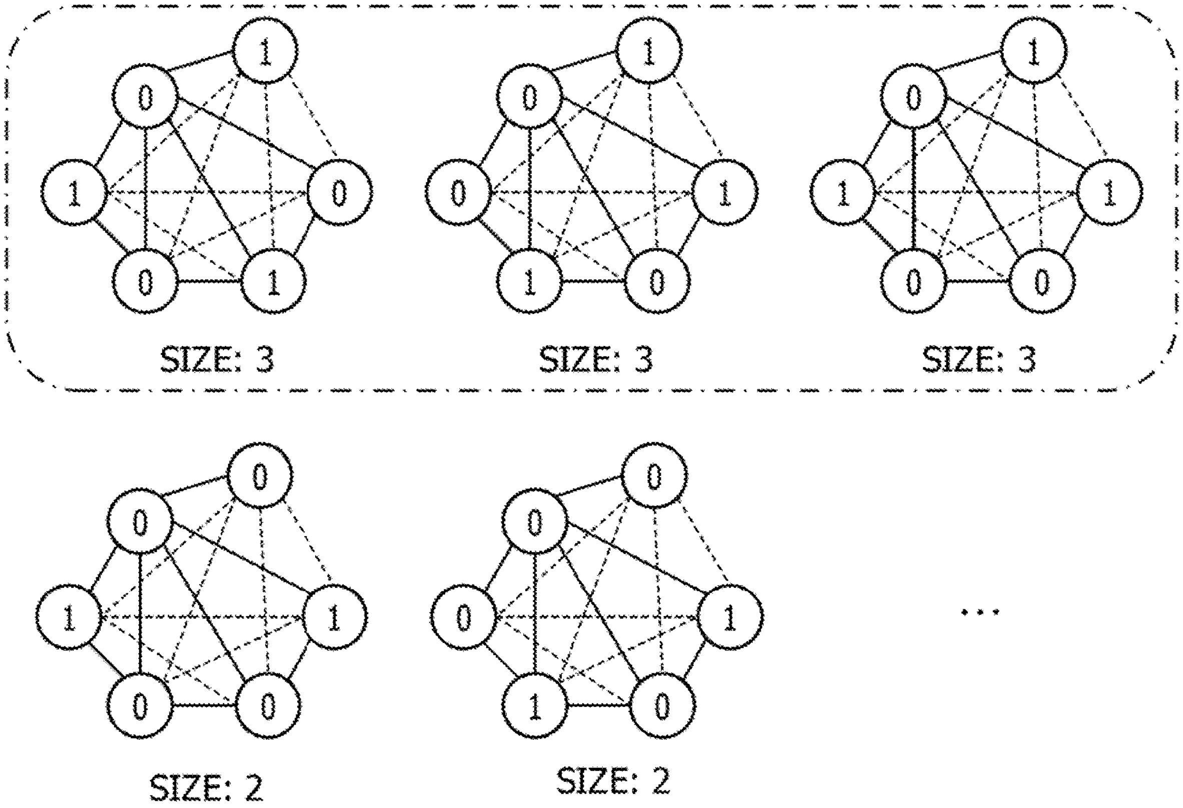
FIG. 5 is a diagram illustrating an example of a maximum independent set in a graph.

FIG. 5 is a diagram illustrating one example of a maximum independent set in a graph. In FIG. 5, a code of "1" is assigned to a node included in a set, a code of "0" is assigned to a node not included in a set, nodes between which an edge exists are linked with each other with a solid line, and nodes between which no edge exists are linked with each other with a dotted line. As illustrated in FIG. 5, for simplicity, description will be given, using graphs each including six number of nodes as an example.

In the example illustrated in FIG. 5, among sets each including nodes each including no edge therein, three sets each include a largest number of nodes, and the number of nodes in each set is three. For example, in the example illustrated in FIG. 5, maximum independent sets in the graph are the three sets surrounded by an alternate long and short dash line.

As described above, the conflict graph is created based on the rule that, when nodes include atoms in different states from each other, an edge is created between the nodes, and when nodes include atoms in the same state, no edge is created between the nodes. For this reason, in a conflict graph, determining a maximum independent set, that is a set including a largest number of nodes, among sets each including nodes each including no edge therein, is synonymous to determining a largest partial structure among common partial structures between two molecules. For example, determining the maximum independent set in the conflict graph makes it possible to determine the largest common partial structure between the two molecules.

For example, by graphing the two molecules, creating the conflict graph based on the structure of the graphed molecules, and determining the maximum independent set in the conflict graph, it is possible to determine the largest common partial structure in the two molecules.

Figure 6:
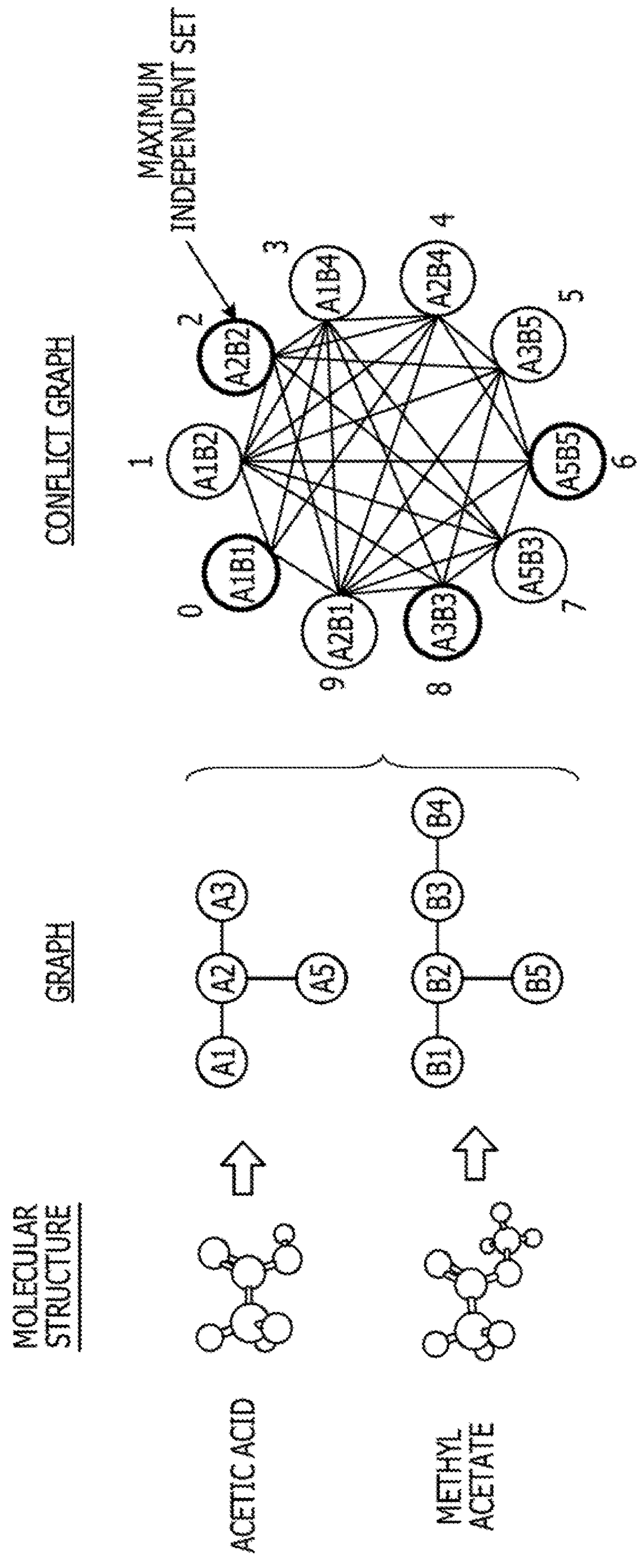
FIG. 6 is a diagram illustrating an example of a flow when a largest common partial structure between the molecule A and the molecule B is determined by determining a maximum independent set of the conflict graph (solving a maximum independent set problem)

FIG. 6 illustrates one example of a flow when a largest common partial structure between a molecule A (acetic acid) and a molecule B (methyl acetate) is determined by determining a maximum independent set of a conflict graph (solving a maximum independent set problem). As illustrated in FIG. 6, the molecule A and the molecule B are each graphed, the same elements are combined to form a node, and an edge is formed according to a state of atoms included in the node, so that a conflict graph is created. Determining a maximum independent set in the created conflict graph makes it possible to determine a largest common partial structure between the molecule A and the molecule B.

One example of a specific method for determining (searching for) a maximum independent set of a conflict graph will be described.

It is possible to search for a maximum independent set of a conflict graph, for example, by using a hamiltonian for which minimizing means searching for a maximum independent set. For example, the search is possible by using a hamiltonian (H) represented by the following formula (1).

$$H = -\alpha\sum_{i=0}^{n-1} b_i x_i + \beta\sum_{i,j=0}^{n-1} w_{ij} x_i x_j \quad (1)$$

In the above formula (1), n is the number of nodes in a conflict graph, and $b_i$ is a numerical value representing a bias for the node ordered i-th.

$w_{ij}$ is a positive number that is not 0 when an edge exists between an i-th node and a j-th node, and is 0 when no edge exists between an i-th node and a j-th node.

$x_i$ is a binary variable indicating that an i-th node is 0 or 1, and $x_j$ is a binary variable indicating that a j-th node is 0 or 1.

α and β are positive numbers.

A relationship between the hamiltonian represented by the above formula (1) and search for a maximum independent set will be described in more detail. The above formula (1) is a hamiltonian representing an Ising model formula in a quadratic unconstrained binary optimization (QUBO) format.

In the above formula (1), $x_i$ means when a value thereof is 1 that an i-th node is included in a set that is a candidate for a maximum independent set, and means when the value thereof is 0 that an i-th node is not included in a set that is a candidate for a maximum independent set. Similarly, in the above formula (1), $x_j$ means when a value thereof is 1 that a j-th node is included in a set that is a candidate for a maximum independent set, and means when the value thereof is 0 that a j-th node is not included in a set that is a candidate for a maximum independent set.

For this reason, with respect to the above formula (1), under a restriction that no edge exists between nodes whose states are each set to 1 (bit is set to 1), it is possible to search for a maximum independent set by searching for a combination with which states of as many nodes as possible result in 1.

Each term in the above formula (1) will be described.

A first term (a term having a coefficient of −α) on a right side in the above formula (1) is a term whose value decreases as the number of Ts each setting $x_i$ to 1 increases (as the number of nodes included in a set that is a candidate for a maximum independent set increases). A decrease in the value the first term on the right side in the above formula (1) means that the value becomes a negative large number. For example, in the above formula (1), due to an action of the first term on the right side, when bits of many nodes are set to 1, a value of the hamiltonian (H) decreases.

A second term on the right side in the above formula (1) (a term having a coefficient of β) is a penalty term whose value increases, when an edge exists between nodes each having a bit of 1 (when $w_{ij}$ is a positive number not 0). For example, the second term on the right side in the above formula (1) is set to 0, when there is no place at which an edge exists between nodes each having a bit of 1, and is set to a positive number in the other cases. For example, in the above formula (1), due to an action of the second term on the right side, when an edge exists between nodes each having a bit of 1, the value of the hamiltonian (H) increases.

As described above, since the value of the above formula (1) decreases when the bits of many nodes are set to 1, and increases when an edge exists between nodes each having a bit of 1, it may be said that minimizing the above formula (1) means searching for a maximum independent set.

A relationship between the hamiltonian represented by the above formula (1) and the search for a maximum independent set will be described with reference to the drawings.

Figure 7:
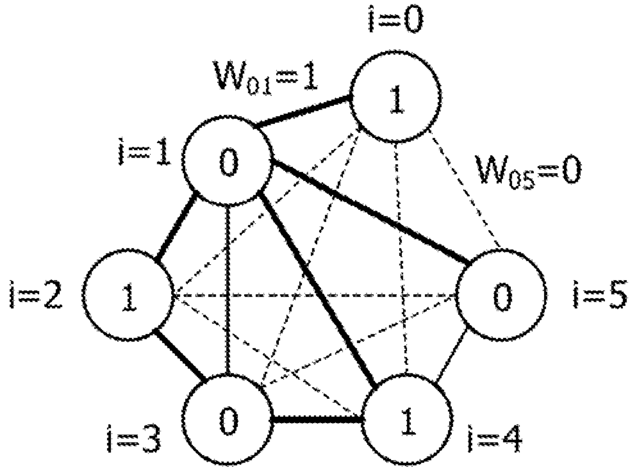
FIG. 7 is an explanatory diagram for explaining an example of a method for searching for a maximum independent set in a graph in which the number of nodes is six.

Considered is a case where a bit is set to each node, as in an example illustrated in FIG. 7, in a graph in which the number of nodes is six. In the example illustrated in FIG. 7, in the same manner as in FIG. 5, nodes between which an edge exists are linked with each other with a solid line, and nodes between which no edge exists are linked with each other with a dotted line.

In the example illustrated in FIG. 7, when $b_i$ in the above formula (1) is set to 1, and $w_{ij}$ is set to 1 when an edge exists between an i-th node and a j-th node, the above formula (1) turns as follows.

$$\begin{aligned} H &= -\alpha(x_0 + x_1 + x_2 + x_3 + x_4 + x_5) + \\ &\quad \beta(w_{01}x_0x_1 + w_{02}x_0x_2 + w_{03}x_0x_3 + w_{04}x_0x_4 + w_{05}x_0x_5 + \ldots) \\ &= -\alpha(1 + 0 + 1 + 0 + 1 + 0) + \\ &\quad \beta(1*1*0 + 0*1*1 + 0*1*0 + 0*1*1 + 0*1*0 + \ldots) \\ &= -3\alpha \end{aligned}$$

In this way, in the example illustrated in FIG. 7, when there is no place at which an edge exists between nodes each having a bit of 1 (when there is no contradiction as an independent set), the second term of the right side becomes 0, and a value of the first term as is becomes the value of the hamiltonian.

Figure 8:
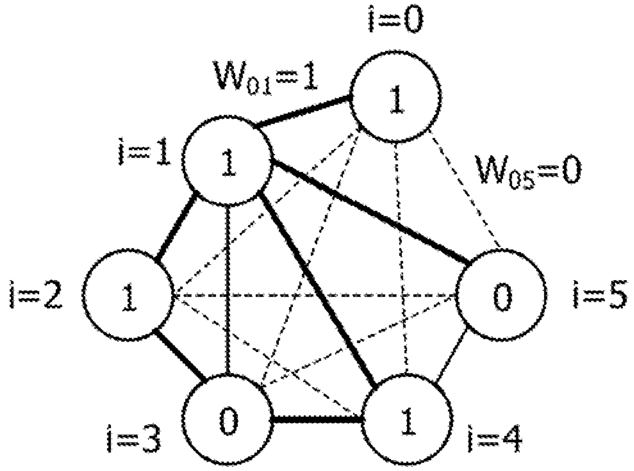
FIG. 8 is an explanatory diagram for explaining an example of the method for searching for a maximum independent set in a graph in which the number of nodes is six.

Next, a case where a bit is set to each node as in an example illustrated in FIG. 8 will be considered. As in the example illustrated in FIG. 7, when $b_i$ in the above formula (1) is set to 1, and $w_{ij}$ is set to 1 when an edge exists between an Rh node and a j-th node, the above formula (1) turns as follows.

$$\begin{aligned} H &= -\alpha(x_0 + x_1 + x_2 + x_3 + x_4 + x_5) + \\ &\quad \beta(w_{01}x_0x_1 + w_{02}x_0x_2 + w_{03}x_0x_3 + w_{04}x_0x_4 + w_{05}x_0x_5 + \ldots) \\ &= -\alpha(1 + 1 + 1 + 0 + 1 + 0) + \\ &\quad \beta(1*1*1 + 0*1*1 + 0*1*0 + 0*1*1 + 0*1*0 + \ldots) \\ &= -4\alpha + 3\beta \end{aligned}$$

In this way, in the example illustrated in FIG. 8, since there is a place at which an edge exists between nodes each having a bit of 1, the second term on the right side does not become 0, and the value of the hamiltonian is a sum of the two terms on the right side. In the example illustrated in each of FIGS. 7 and 8, for example, α>5β leads to −3α<−4α+5β, so that the value of the hamiltonian in the example of FIG.

7 is smaller than the value of the hamiltonian in the example of FIG. 8. The example illustrated in FIG. 7 is a set of nodes having no contradiction as a maximum independent set, it may be seen that by searching for a combination of nodes decreasing the value of the hamiltonian in the above formula (1), it is possible to find a maximum independent set.

Next, in one example of the related art described in Non-Patent Document 1, a method of calculating a degree of similarity in structure between molecules, based on a found maximum independent set will be described.

The degree of similarity in structure between molecules may be calculated by using, for example, the following formula (2).

$$S(G_A, G_B) = \delta\max\left\{\frac{|V_C^A|}{|V_A|}, \frac{|V_C^B|}{|V_B|}\right\} + (1-\delta)\min\left\{\frac{|V_C^A|}{|V_A|}, \frac{|V_C^B|}{|V_B|}\right\} \quad (2)$$

In the above formula (2), $S(G_A, G_B)$ represents a degree of similarity between a graphed first molecule (for example, a molecule A) and a graphed second molecule (for example, a molecule B), is represented by 0 to 1, and means that the degree of similarity is higher as $S(G_A, G_B)$ approaches 1.

$V_A$ represents a total number of node atoms in the graphed first molecule, and $V_C^A$ represents the number of node atoms included in a maximum independent set of a conflict graph among node atoms in the graphed first molecule. A node atom means an atom at a vertex in a graphed molecule.

$V_B$ represents a total number of node atoms in the graphed second molecule, and $V_C^B$ represents the number of node atoms included in a maximum independent set of the conflict graph among node atoms in the graphed second molecule.

$\delta$ is the number of 0 to 1.

In the above formula (2), max{A, B} means, from A and B, selecting one having a larger value, and min{A, B} means, from A and B, selecting one having a smaller value.

A method for calculating a degree of similarity will be described using acetic acid (molecule A) and methyl acetate (molecule B) as an example, as in the case of FIG. 1 and the like.

Figure 9:
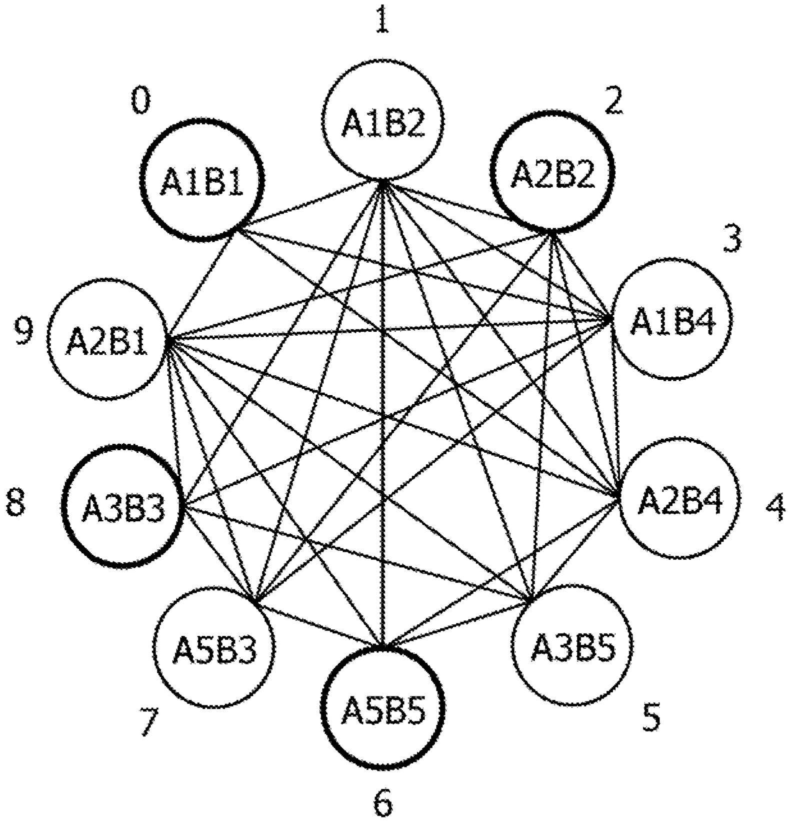
FIG. 9 is a diagram illustrating an example of a maximum independent set in the conflict graph.

In a conflict graph illustrated in FIG. 9, a maximum independent set is composed of four nodes, namely, the node [A1B1], the node [A2B2], the node [A3B3], and the node [A5B5]. For example, in the example illustrated in FIG. 9, $|V_A|$ is 4, $|V_C^A|$ is 4, $|V_B|$ is 5, and $|V_C^B|$ is 4. In this example, when $\delta$ is set to 0.5 to obtain an average of the first molecule and the second molecule (handle equally), the above formula (2) turns as follows.

$$\begin{aligned} S(G_A, G_B) &= 0.5*\max\left\{\frac{4}{5}, \frac{4}{5}\right\} + (1-0.5)*\min\left\{\frac{4}{4}, \frac{4}{5}\right\} \\ &= 0.5*\frac{4}{4} + (1-0.5)*\frac{4}{5} = 0.9 \end{aligned}$$

In this way, in the example illustrated in FIG. 9, based on the above formula (2), a degree of similarity in structure between molecules is calculated to be 0.9.

As described above, in the one example of the related art described in Non-Patent Document 1, by using the above formulas (1) and (2), a degree of similarity in structure between compounds (molecules) is calculated.

However, in the related art described above, the degree of similarity is calculated, based only on structural information on the compound. Thus, when, based on a degree of similarity in structure calculated using the above related art, trying to predict a characteristic value of a characteristic (physical property) of a compound, there was a case in which prediction accuracy may deteriorate depending on a characteristic to be predicted. For example, a relative permittivity of a compound is a characteristic affected by polarizability of the compound, or the like, and it may be difficult to accurately calculate the relative permittivity based only on information on simple structure of the compound.

In the related art described above, there was a problem that it is not possible to calculate a degree of similarity of a compound for each characteristic to be predicted, and it is not possible to search for a similar compound by focusing on a desired characteristic. For example, in the related art, a degree of similarity is calculated based only on structural information on a compound, thus, for example, the same compound is evaluated to have a high degree of similarity (having characteristic values close to each other) both when a boiling point is predicted and when a heat transfer coefficient is predicted. However, in practice, respective heat transfer coefficients of compounds having respective boiling points close to each other are not necessarily close to each other.

In this way, in the related art, it was not possible to find a similar compound according to a characteristic to be predicted.

Thus, the inventors have devised the technique disclosed herein, by extensively studying a bonding structure search apparatus or the like capable of predicting a characteristic value of a characteristic of a target material such as a compound, with high accuracy in accordance with the characteristic. For example, the inventors have found that, when predicting a characteristic value of a characteristic of a target material, by determining a degree of similarity according to the characteristic between a target material and a first material whose characteristic value of the characteristic is a first value, to predict a characteristic value of the target material, it is possible to predict the characteristic value of the target material with high accuracy.

Hereinafter, one example of the technique disclosed herein will be described.

Target Material, First Material

In the one example of the technique disclosed herein, a target material means a material whose characteristic value is predicted. As the target material, for example, a material whose characteristic value of a characteristic to be predicted is unknown may be used.

The target material is not particularly limited, may be appropriately selected depending on a purpose, and may or may not be a molecule. Examples of the target material other than the molecule include, for example, inorganic crystals, or the like.

When a characteristic value is predicted by solving a maximum independent set problem in a conflict graph, a target material is not particularly limited as long as the material may be graphed, and may be appropriately selected according to a purpose.

In the one example of the technique disclosed herein, a first material means a material whose characteristic value of a characteristic to be predicted in a target material is a first value. The first value is not particularly limited, may be appropriately selected according to a purpose, and for example, a characteristic value already known may be used. For example, the first material may be, for example, a material whose characteristic value of a characteristic to be predicted in a target material is specified (known).

The first material is not particularly limited, may be appropriately selected depending on a purpose, and may be similar material to the target material, for example.

In the one example of the technique disclosed herein, chemical structure data of the target material is preferably inputted as a chemical structure data group (database) of a large number of the target materials. For example, a material characteristic prediction apparatus as the one example of the technique disclosed herein preferably includes a chemical structure data group of a large number of the target materials. Similarly, the material characteristic prediction apparatus as the one example of the technique disclosed herein preferably includes a chemical structure data group of a large number of the first materials.

A format (data structure) of the chemical structure data group of each of the target materials and the first materials is not particularly limited, may be appropriately selected depending on a purpose, and for example, examples thereof include the SDF format described above. In the one example of the technique disclosed herein, for example, based on information on a characteristic of a target material included in the chemical structure data group of the first materials, it is possible to determine a degree of similarity according to the characteristic.

In the one example of the technique disclosed herein, for example by accepting a compound name or a customary name of a target material, and checking the name against the chemical structure data group of the target materials, structure of the target material may be specified. In the one example of the technique disclosed herein, for example, by directly inputting chemical structure data of a target material, structure of the target material may be specified.

In the one example of the technique disclosed herein, as appropriate, a chemical structure database of target materials may be updated, by adding new chemical structure data. Similarly, in the one example of the technique disclosed herein, as appropriate, a chemical structure database of first materials may be updated, by adding new chemical structure data.

Characteristic of Material

A characteristic of a target material to be predicted using the one example of the technique disclosed herein is not particularly limited, may be appropriately selected according to a purpose, and for example, examples thereof include a relative permittivity, a boiling point, a melting point, a heat transfer coefficient, specific heat, viscosity, a vapor pressure, vaporization heat, a flash point, and the like. When activity for a specific substance (for example, a bonding property, reactivity, or the like) is known for a first material, such activity may be predicted by using the one example of the technique disclosed herein.

Degree of Similarity According to Characteristic

In the one example of the technique disclosed herein, a degree of similarity according to a characteristic is determined. For example, the material characteristic prediction apparatus as the one example of the technique disclosed herein includes a characteristic prediction unit for determining a degree of similarity according to a characteristic, between a target material and a first material, to predict a characteristic value of the target material.

Hereinafter, one example of a method for determining a degree of similarity according to a characteristic, in the technique disclosed herein will be described. In the material characteristic prediction apparatus as the one example of the technique disclosed herein, it is possible to perform calculation of a degree of similarity according to a characteristic, and prediction of a characteristic value of a target material by, for example, the characteristic prediction unit included in the material characteristic prediction apparatus.

In the one example of the technique disclosed herein, for example, when determining a degree of similarity between a target material and a first material, by using the above formula (1) and formula (2), parameters in the above formula (1) and formula (2) are optimized so as to improve prediction accuracy of a characteristic value of the target material to be predicted.

In the one example of the technique disclosed herein, for example similar to the related art described above, by using the formula (1) to search for a maximum independent set based on respective molecular structures of a target material and a first material, it is possible to determine a degree of similarity according to a characteristic.

$$H = -\alpha\sum_{i=0}^{n-1} b_i x_i + \beta\sum_{i,j=0}^{n-1} w_{ij} x_i x_j \quad (1)$$

In the above formula (1), H is the hamiltonian, for which minimizing means searching for a maximum independent set.

n is understood as the number of nodes a conflict graph of graphed target material and first material.

The conflict graph is understood to be a graph that is created based on a rule that, a combination of each node atom constituting the graphed target material and each node atom constituting the graphed first material is defined as a node, and when multiple nodes are compared with each other and determined not to be identical to each other, an edge is created between the nodes, and when multiple nodes are compared and determined to be identical to each other, no edge is created between the nodes.

$b_i$ is a numerical value representing a bias for an i-th node.

$w_{ij}$ is a positive number that is not 0 when an edge exists between an i-th node and a j-th node, and is 0 when no edge exists between an i-th node and a j-th node.

$x_i$ is a binary variable representing that an i-th node is 0 or 1, and $x_j$ is a binary variable representing that a j-th node is 0 or 1.

α and β are positive numbers.

In the one example of the technique disclosed herein, "multiple nodes are compared and determined to be identical to each other" means that multiple nodes are compared with each other and determined to be composed of node atoms that are in the same state (bonding state). Similarly, in the one example of the technique disclosed herein, "multiple nodes are compared and determined not to be identical to each other" means that multiple nodes are compared with each other and determined to be composed of node atoms that are in different states from each other (bonding state).

In the one example of the technique disclosed herein, when searching for a maximum independent set using the above formula (1), it is not mandatory to create a conflict graph of a target material and a first material, and it is sufficient that at least it is possible to minimize the above formula (1). For example, in the one example of the technique disclosed herein, searching for a maximum independent set in a conflict graph of a target material and a first material is solved by replacing the search with a combination optimization problem in a hamiltonian for which minimizing means searching for a maximum independent set. It is possible to perform minimization of a hamiltonian represented by an Ising model formula in a QUBO format, as in the above formula (1), in a short time by using an annealing machine or the like and performing an annealing method.

Thus, in the one aspect of the technique disclosed herein, by using the above formula (1), it is possible to search for a maximum independent set by an annealing method using an annealing machine or the like, thereby predicting a characteristic value of a target material in a shorter time. For example, in the one aspect of the technique disclosed herein, by minimizing the hamiltonian (H) in the above formula (1) with an annealing method to search for a maximum independent set, it is possible to predict a characteristic value of a target material in a shorter time. The annealing method will be described in detail later.

In the one example of the technique disclosed herein, for example similar to the related art described above, by using the formula (2), it is possible to determine a degree of similarity according to a characteristic for a found maximum independent set.

$$S(G_A, G_B) = \delta\max\left\{\frac{|V_C^A|}{|V_A|}, \frac{|V_C^B|}{|V_B|}\right\} + (1-\delta)\min\left\{\frac{|V_C^A|}{|V_A|}, \frac{|V_C^B|}{|V_B|}\right\} \quad (2)$$

In the above formula (2), $G_A$ represents a graphed target material, $G_B$ represents a graphed first material, $S(G_A, G_B)$ represents a degree of similarity between the graphed target material and the graphed first material, is represented by 0 to 1, and means that the degree of similarity is higher as $S(G_A, G_B)$ approaches 1.

$V_A$ represents a total number of node atoms in the graphed target material, and $V_C^A$ represents the number of node atoms included in a maximum independent set of a conflict graph among node atoms in the graphed target material.

$V_B$ represents a total number of node atoms in the graphed first material, and $V_C^B$ represents the number of node atoms included in the maximum independent set of the conflict graph among node atoms in the graphed first material.

δ is the number of 0 to 1.

In one aspect of the technique disclosed herein, by using the above formula (2) to determine a degree of similarity according to a characteristic for a found maximum independent set, based on a maximum independent set found by using the above formula (1), it is possible to determine a degree of similarity according to a characteristic between a target material and a first material.

Next, as one example of the technique disclosed herein, a case will be described in which, when the above formula (1) is used to determine a degree of similarity according to a characteristic, a label is added to a node atom in each of graphed target material and first material, in consideration of information on coupling node atoms to each other. As described above, a node atom means an atom at vertex in graphed target material and first material.

The method of adding a label in consideration of information on coupling node atoms to each other is not particularly limited, may be appropriately selected according to a purpose, and for example, may be performed by a Weisfeiler-Lehman procedure disclosed in Shervashidze Nino, Schweitzer Pascal, Jan van Leeuwen Erik, Mehlhorn Kurt, Borgwardt Karsten M., "Weisfeiler-Lehman Graph Kernels", Journal of Machine Learning Research, 2539-2561, 2011.

The Weisfeiler-Lehman procedure means, for example, a procedure in which a label to be added to a node atom in each of graphed target material and first material is relabeled (the label is re-assigned) in consideration of a label of a node atom to which that node atom is coupled (bonded). In the following description, a label added to a node atom by performing the Weisfeiler-Lehman procedure may be referred to as a "WL label".

For example, by adding a WL label according to the Weisfeiler-Lehman procedure to a node atom, it is possible to include, into a label of a node atom, information on node atoms existing around the node atom. Accordingly, in one aspect of the technique disclosed herein, when the formula (1) is used to determine a degree of similarity according to a characteristic, by adding a WL label to a node atom, it is possible to add the label in consideration of a state of the node atom. For example, in order to enhance correlation between a characteristic value in a first material and a degree of similarity between a target material and the first material, by adding a WL label to each node atom to determine a degree of similarity according to a characteristic, it is possible to predict a characteristic value of the target material with higher accuracy.

In one example of the technique disclosed herein, the number of times the Weisfeiler-Lehman procedure is performed on a node atom is not particularly limited, may be appropriately selected according to a purpose, and may be one, or plural. In the Weisfeiler-Lehman procedure, every time a relabeling is performed, it is possible to include information on a farther node atom in the relabeled node atom.

Figure 10:
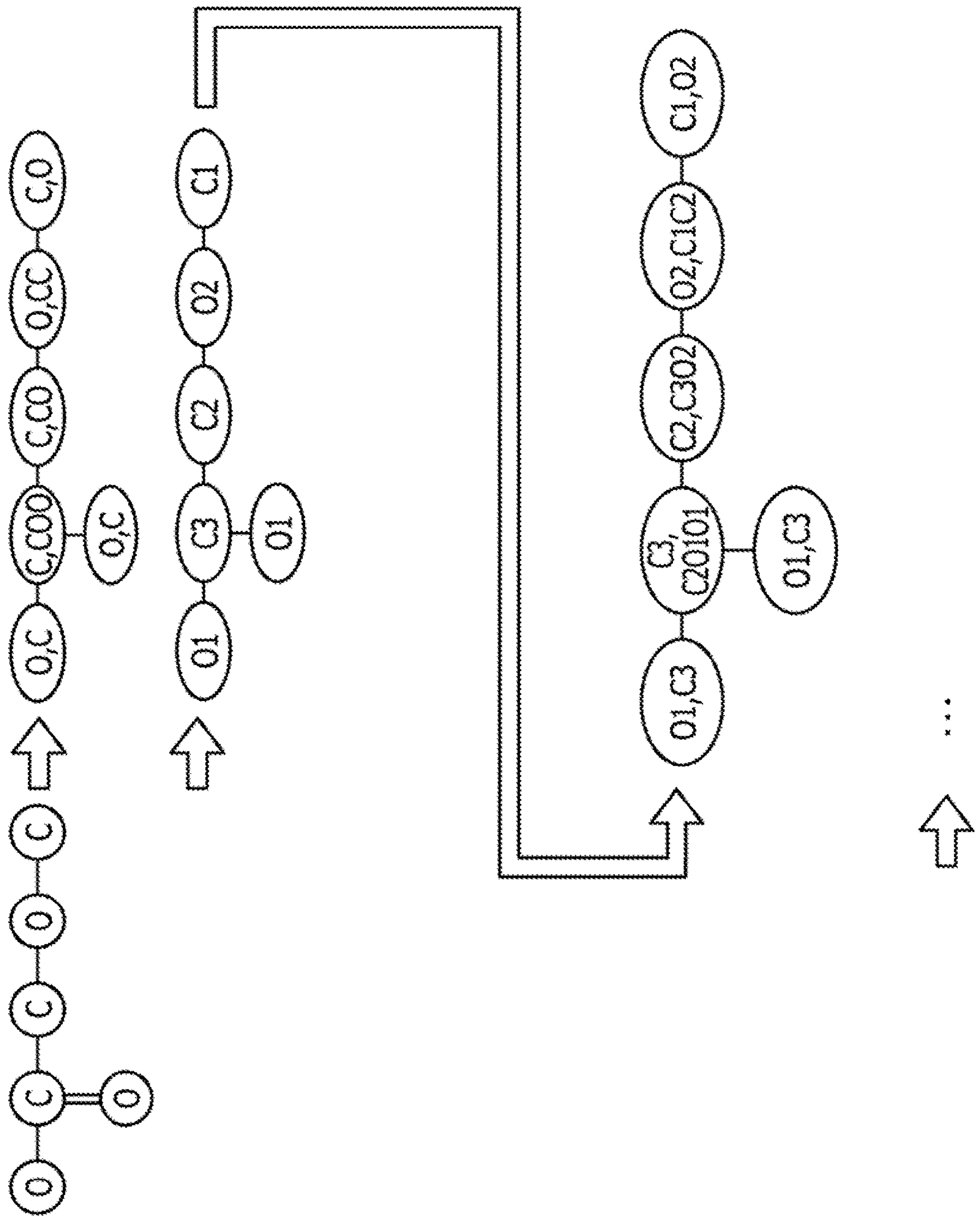
FIG. 10 is a schematic diagram illustrating an example of a flow when a Weisfeiler-Lehman procedure is performed to add a WL label to a node atom.

FIG. 10 is a schematic diagram illustrating one example of a flow when the Weisfeiler-Lehman procedure is performed and a WL label is added to a node atom. In the example illustrated in FIG. 10, a description will be given of a case where the Weisfeiler-Lehman procedure is performed for graphed methoxyacetic acid ($CH_3OCH2COOH$) and add a WL label.

In structure of methoxyacetic acid graphed by selecting atoms other than hydrogen atoms, as illustrated in a left part of FIG. 10, to each node atom, a type (element) of the node atom is added as a label A state is illustrated in a central part of FIG. 10 in which, a WL label is added to this graphed structure of methoxyacetic acid, by performing relabeling once according to the Weisfeiler-Lehman procedure. In the example illustrated on an upper side of the central part of FIG. 10, for example, a WL label added to carbon in carboxyl group is [C, COO]. This WL label of [C, COO] is a label that means that a node atom to which the WL label is added is a carbon atom bonded to one carbon atom and two oxygen atoms.

On a lower side of the central part of FIG. 10, a WL label illustrated on the upper side of the central part of FIG. 10 is rewritten, for each type of contents of the WL label, and illustrated. For example, for a node atom to which a WL label of [O, C] is added on the upper side of the central part of FIG. 10, the WL label is rewritten to a WL label of [O1] on the lower side of the central part of FIG. 10. As described above, by rewriting the WL label, it is possible to simplify the notation of the WL label.

In a right part of FIG. 10, a state is illustrated in which, the Weisfeiler-Lehman procedure is further performed for structure illustrated on the lower side of the central part of FIG. 10, and a WL label is added in a second labelling. In the example illustrated in the right part of FIG. 10, for example, a WL label of [O1, C3] is a label that means that a node atom to which the WL label is added is a node atom of O1 bonded to a node atom of C3.

In the example illustrated in FIG. 10, a case was described in which, when rewriting notation of a WL label, or performing the Weisfeiler-Lehman procedure multiple times, information of a previous state is lost, but the technique disclosed herein is not limited thereto. For example, in the one example of the technique disclosed herein, when performing relabeling multiple times, information of a previous state (information of a WL label before relabeling) may also be included in the WL label after the relabeling.

In the one example of the technique disclosed herein, it is preferable that a WL label be, in one node atom in node atoms, derived from information on the one node atom and information on a bonded node atom to which the one node atom is bonded. For example, in the one example of the technique disclosed herein, a WL label is preferably added to a node atom by performing the Weisfeiler-Lehman procedure once.

In this way, in one aspect of the technique disclosed herein, since it is possible to, into a WL label of each node atom, include information on a node atom to which the node atom is bonded, it is possible to appropriately consider circumstances around the node atom, and add a WL label.

In one example of the technique disclosed herein, information included in a WL label is not particularly limited, and may be appropriately selected according to a purpose. The information included in a WL label may be, for example, a type (element) of node atom as in the example described above, or may be a contribution value to expression of a characteristic to be predicted.

In the one example of the technique disclosed herein, a contribution value (ΔB) to expression of a characteristic to be predicted means a numerical value that serves as a criterion for calculating a value of an evaluation index (B) included in information on a WI label added to a node atom constituting an i-th node in the above formula (1).

In the one example of the technique disclosed herein, the contribution value ΔB to expression of a characteristic to be predicted is calculated, for example, for each type (element) of a node atom in each of a target material and a first material. For example, in the one example of the technique disclosed herein, an evaluation index B, means a sum of the contribution value ΔB to expression of a characteristic, calculated for each type (element) of a node atom in each of a target material and a first material.

As a contribution value ΔB to expression of a characteristic to be predicted, for example, a numerical value is preferably selected such that a correlation coefficient between a degree of similarity according to a characteristic and a characteristic value according to the characteristic increases. A specific method of setting a contribution value ΔB to a numerical value such that a correlation coefficient between a degree of similarity according to a characteristic and a characteristic value according to the characteristic increases will be described later.

In the one example of the technique disclosed herein, when the above formula (1) is used to determine a degree of similarity according to a characteristic, a node atom is preferably selected according to an evaluation index $B_i$ to expression of a characteristic according to information on a WL label. For example, in the one example of the technique disclosed herein, a node that may be included in a maximum independent set in a conflict graph is preferably selected according to an evaluation index $B_i$.

In this manner, in one aspect of the technique disclosed herein, it is possible to appropriately select a node atom to be used for calculating a degree of similarity that contributes to expression of a characteristic, thereby predicting a characteristic value of a target material with high accuracy.

It is possible to select a node atom according to an evaluation index $B_i$, for example, by selecting a node atom whose evaluation index $B_i$ exceeds a threshold value. For example, in one example of the technique disclosed herein, when the formula (1) is used to determine a degree of similarity according to a characteristic, it is possible to select a node atom when an evaluation index $B_i$ exceeds a threshold value.

The threshold value for an evaluation index $B_i$ is not particularly limited, and may be appropriately selected according to a purpose, but a numerical value is preferably set such that a correlation coefficient between a degree of similarity according to a characteristic and a characteristic value according to the characteristic increases. For example, in the one example of the technique disclosed herein, a threshold value of an evaluation index $B_i$ included in information on a WL label added to a node atom constituting an i-th node is preferably set to a numerical value such that a correlation coefficient between a degree of similarity according to a characteristic and a characteristic value according to the characteristic increases, in formula (1). A specific method of setting a threshold value of an evaluation index $B_i$ to a numerical value such that a correlation coefficient between a degree of similarity according to a characteristic and a characteristic value according to the characteristic increases will be described later.

In the one example of the technique disclosed herein, a node atom selected according to the method described above, or the like, may be used to create a node of a conflict graph. In this manner, in one aspect of the technique disclosed herein, it is possible to reduce the number of nodes in a conflict graph, thereby reducing the number of bits of a calculator demanded for searching for a maximum independent set.

In one example of the technique disclosed herein, a conflict graph including all combinations of node atoms in a target material and a first material may be created, such that a node containing a node atom selected by the method described above, or the like, may be included in a maximum independent set. For example, in the one example of the technique disclosed herein, a maximum independent set may be searched for nodes including node atoms selected by the method described above, or the like.

In the one example of the technique disclosed herein, a method of searching for a maximum independent set for nodes including node atoms selected according to the method described above, or the like, is not particularly limited, and may be appropriately selected according to a purpose.

It is possible to perform the searching for a maximum independent set for nodes including selected node atoms by, for example, setting $b_i$ in the above formula (1) to a numerical value corresponding to magnitude of an evaluation index $B_i$ included in information on a WL label added to a node atom constituting an i-th node. It is possible to perform the setting $b_i$ in the above formula (1) to a numerical value corresponding to magnitude of an evaluation index $B_i$ by, for example, adapting to a magnitude relation between a numerical value of $b_i$ in the above formula (1) and a numerical value of an evaluation index $B_i$. For example, it is possible to perform the adapting by increasing a numerical value of $b_i$ in a node having a large numerical value of an evaluation index $B_i$, and decreasing a numerical value of $b_i$ in a node having a small numerical value of an evaluation index $B_i$.

In this manner, in one aspect of the technique disclosed herein, it is possible to search for a maximum independent set such that a node having a node atom having a large evaluation index $B_i$ that is regarded to contribute to expression of a characteristic is included. Accordingly, the one aspect of the technique disclosed herein, it is possible to appropriately consider an atom that contributes to expression of a characteristic, and determine a degree of similarity according to a characteristic, thereby predicting a characteristic value of a target material with higher accuracy.

Searching for a maximum independent set for nodes including selected node atoms may be performed by, for example, determining $b_i$ in the formula (1) according to the following condition.

Condition $b_i$ in formula (1) is set to a positive number, when an evaluation index $B_i$ included in information on a WL label added to a node atom constituting an i-th node exceeds a threshold value, and is set to a negative number, when an evaluation index $B_i$ included in information of a WL label added to a node atom constituting an i-th node is equal to or less than a threshold value.

In a case where $b_i$ is a positive number (a number larger than 0) in the above formula (1), a value of the first term (a term having a coefficient of $-\alpha$) on the right side in the above formula (1) decreases, when an i-th node is included in an independent set (when a bit of the i-th node is 1). For example, in the case where $b_i$ is a positive number in the above formula (1), due to an action of the first term on the right side, when the i-th node is included in the independent set, a value of the hamiltonian (H) decreases. This corresponds to searching for a maximum independent set such that the i-th node is included.

On the other hand, in a case where $b_i$ is a negative number (a number smaller than 0) in the above formula (1), a value of the first term on the right side in the above formula (1) increases, when an i-th node is included in an independent set (when a bit of the i-th node is 1). For example, in the case where $b_i$ is a negative number in the above formula (1), due to an action of the first term on the right side, when the i-th node is included in the independent set, a value of the hamiltonian (H) increases. This corresponds to searching for a maximum independent set such that the i-th node is excluded.

As described above, based on a threshold value of an evaluation index $B_i$, by changing positive and negative of $b_i$ in the above formula (1), it is possible to search for a maximum independent set such that a node having a node atom whose evaluation index $B_i$ exceeds a threshold value that is regarded to contribute to expression of a characteristic is included. Accordingly, in the one aspect of the technique disclosed herein, it is possible to consider more appropriately an atom that contributes to expression of a characteristic to determine a degree of similarity according to a characteristic, thereby predicting a characteristic value of a target material with higher accuracy.

Magnitude of a numerical value when $B_i$ in the above formula (1) is a positive number is not particularly limited, may be appropriately selected according to a purpose, and may be set to 1, for example. Similarly, magnitude of a numerical value when $b_i$ in the above formula (1) is a negative number is not particularly limited, may be appropriately selected according to a purpose, and may be set to $-1$, for example.

In the above description, as the one example of the technique disclosed herein, the selection of a contribution value $\Delta B$ and a threshold value of an evaluation index $B_i$ for each type (element) of node atom to increase a correlation coefficient between a degree of similarity according to a characteristic and characteristic value according to the characteristic has been described. However, the techniques disclosed herein are not limited to the above embodiments, and an embodiment may be adopted in which other parameters and the like are selected (updated) such that a correlation coefficient between a degree of similarity according to a characteristic and a characteristic value according to the characteristic increases.

For example, in one example of the technique disclosed herein, it is preferable to update at least one of the following parameters i) to iv), and a formula itself of a similarity degree evaluation formula S in v), such that a correlation coefficient once determined between a degree of similarity according to a characteristic and a characteristic value according to the characteristic increases.

i) A numerical value of a contribution value $\Delta B$ for each type (element) of a node atom, that serves as a criterion for calculating a value of an evaluation index $B_i$ included in information on a WL label added to a node atom constituting an i-th node, in the above formula (1)

ii) A threshold value of an evaluation index $B_i$ included in information on a WL label added to a node atom constituting an i-th node, in the above formula (1)

iii) A numerical value of $b_i$ in the above formula (1)

iv) A numerical value of $w_{ij}$ in the above formula (1)

v) The similarity degree evaluation formula S represented by the above formula (2)

For example, in the one example of the technique disclosed herein, it is preferable to update at least one of the above i) to v) such that a correlation coefficient determined between a degree of similarity according to a characteristic and a characteristic value according to the characteristic increases, and to recalculate the degree of similarity according to the characteristic. In this way, in one aspect of the technique disclosed herein, it is possible to optimize parameters for calculating a degree of similarity according to a characteristic, and predict a characteristic value of a target material with higher accuracy.

A description will be given of a case where the similarity degree evaluation formula S represented by the above formula (2) of above v) is updated. The update of the similarity degree evaluation formula S in the above v) is not particularly limited, may be appropriately selected according to a purpose, for example, and examples thereof include selection of a formula used for calculation of a degree of similarity from a plurality of the similarity degree evaluation formulas S, update of a numerical value of δ in the similarity degree evaluation formula S, and the like.

In one example of the technique disclosed herein, for example, it is also possible to select the following formula from among a plurality of the similarity degree evaluation formulas S to update the similarity degree evaluation formula S represented by the formula (2), such that a correlation coefficient determined between a degree of similarity according to a characteristic and a characteristic value according to the characteristic increases.

$$S(G_A, G_B) = \delta_1 \max\left\{\frac{|V_c^A|}{|V_A|}, \frac{|V_c^B|}{|V_B|}\right\} + \delta_2 \min\left\{\frac{|V_c^A|}{|V_A|}, \frac{|V_c^B|}{|V_B|}\right\} + \delta_3 \min\left\{\frac{M_A}{M_B}, \frac{M_B}{M_A}\right\}$$

In the above formula, $M_A$ represents molecular weight of a target material, $M_B$ represents molecular weight of a first material, and $\delta_1+\delta_2+\delta_3=1$.

For example, when predicting a boiling point in a target material, and molecular weight greatly affects the prediction of a boiling point, it is conceivable that by updating the similarity degree evaluation formula S represented by the above formula (2) to the above formula, it is possible to improve accuracy of the prediction of a boiling point.

By updating $\delta_1$, $\delta_2$, and $\delta_3$ of the above formula such that a correlation coefficient determined between a degree of similarity according to a characteristic and a characteristic value according to the characteristic increases, it is possible to further improve the accuracy of the prediction of a boiling point. When molecular weight greatly affects the prediction of a boiling point, it is conceivable that by updating and optimizing $\delta_1$, $\delta_2$, and $\delta_3$ of the above formula, $\delta_3$ is set to be a value larger than $\delta_1$ and $\delta_2$.

The method of updating at least one of the above parameters i) to v) is not particularly limited, may be appropriately selected according to a purpose, and for example, machine learning may be used. A specific machine learning method is not particularly limited, and may be appropriately selected according to a purpose, but it is preferable to use a genetic algorithm.

A genetic algorithm is a method of preparing a plurality of "individuals" each express data (solution candidate) by genes, preferentially selecting an individual having high fitness, and searching for a solution while repeating operations such as crossover (recombination) and mutation.

In one aspect of the technique disclosed herein, by updating at least one of the above parameters i) to v) according to genetic algorithm, it is possible to improve a correlation coefficient more effectively between a degree of similarity according to a characteristic and a characteristic value according to the characteristic.

In one example of the technique disclosed herein, when a correlation coefficient determined between a degree of similarity according to a characteristic and a characteristic value according to the characteristic exceeds a threshold value, the degree of similarity according to the characteristic in a target material is preferably outputted. In this manner, in one aspect of the technique disclosed herein, in a state where parameters for calculating a degree of similarity according to a characteristic are optimized, it is possible to output the degree of similarity according to a characteristic.

A threshold value in a correlation coefficient determined between a degree of similarity according to a characteristic and a characteristic value according to the characteristic is not particularly limited, may be appropriately selected according to a purpose, and may be set to 0.7, for example.

In one example of the technique disclosed herein, when a correlation coefficient determined between a degree of similarity according to a characteristic and a characteristic value according to the characteristic exceeds a threshold value, a characteristic value in a target material is preferably predicted. In this manner, in one aspect of the technique disclosed herein, in a state where parameters for calculating a degree of similarity according to a characteristic are optimized, by using the degree of similarity according to a characteristic, it is possible to predict a characteristic value of a target material with higher accuracy.

One example of the technique disclosed herein will be described in more detail, with reference to configuration examples of the apparatus, flowcharts, and the like.

Figure 11:
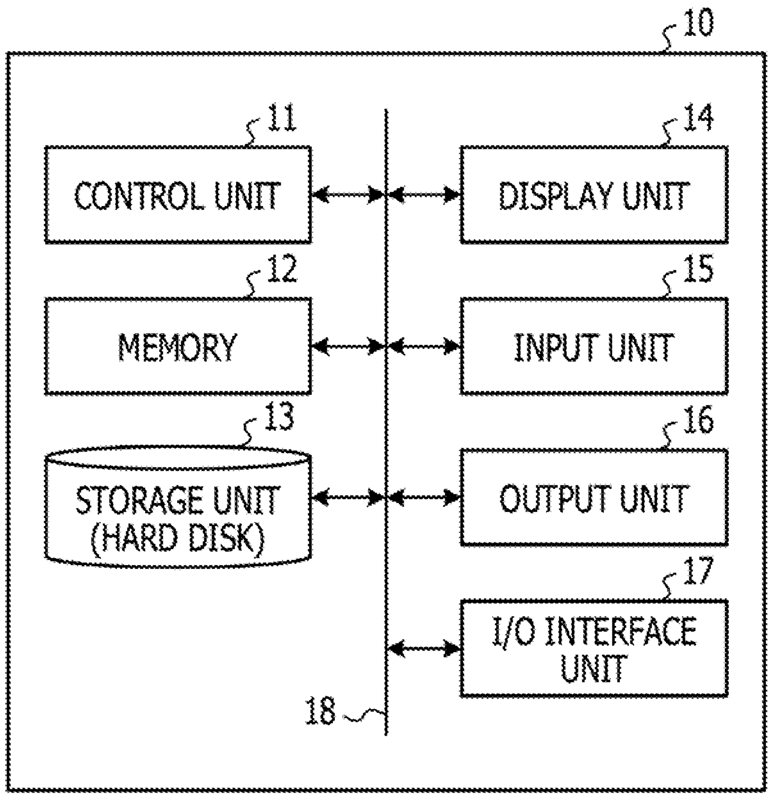
FIG. 11 is a diagram illustrating a configuration example of a material characteristic prediction apparatus disclosed herein.

FIG. 11 illustrates a hardware configuration example of the material characteristic prediction apparatus disclosed herein.

In a material characteristic prediction apparatus 10, for example, a control unit 11, a memory 12, a storage unit 13, a display unit 14, an input unit 15, an output unit 16, and an I/O interface unit 17 are coupled to each other via a system bus 18.

The control unit 11 performs operations (four arithmetic operations, comparison operations, operations for an annealing method, and the like), operation control of hardware and software, and the like.

The control unit 11 is not particularly limited, and may be appropriately selected according to a purpose, and may be, for example, a processor which includes a central processing unit (CPU) or an optimization apparatus used in an annealing method to be described later, and may be a combination thereof. The CPU may be a single CPU, a multi CPU, or a multi-core CPU.

A characteristic prediction unit in the material characteristic prediction apparatus disclosed herein may be realized by, for example, the control unit 11.

The memory 12 is a memory such as a random-access memory (RAM) or a read-only memory (ROM). The RAM stores an operating system (OS), an application program, and the like, read from the ROM and the storage unit 13, and functions as a main memory and a work area of the control unit 11.

The storage unit 13 is a device for storing various programs and data, and is a hard disk, for example. The storage unit 13 stores a program to be executed by the control unit 11, data demanded for execution of the program, the OS, and the like.

A material characteristic prediction program disclosed herein is, for example, stored in the storage unit 13, loaded into the RAM (main memory) of the memory 12, and executed by the control unit 11. The material characteristic prediction program may be divided into a plurality of programs.

The display unit 14 is a display device, and is, for example, a display device such as a cathode-ray tube (CRT) monitor, or a liquid crystal panel.

The input unit 15 is an input device for various data, and is, for example, a keyboard, a pointing device (for example, a mouse, or the like), or the like.

The output unit 16 is an output device for various data, and is, for example, a printer, or the like.

The I/O interface unit 17 is an interface for coupling various external devices. The I/O interface unit 17 allows input/output of data such as a compact disc read-only memory (CD-ROM), a digital versatile disk read-only memory (DVD-ROM), a magneto-optical (MO) disk, and a Universal Serial Bus (USB) memory [flash drive], for example.

Figure 12:
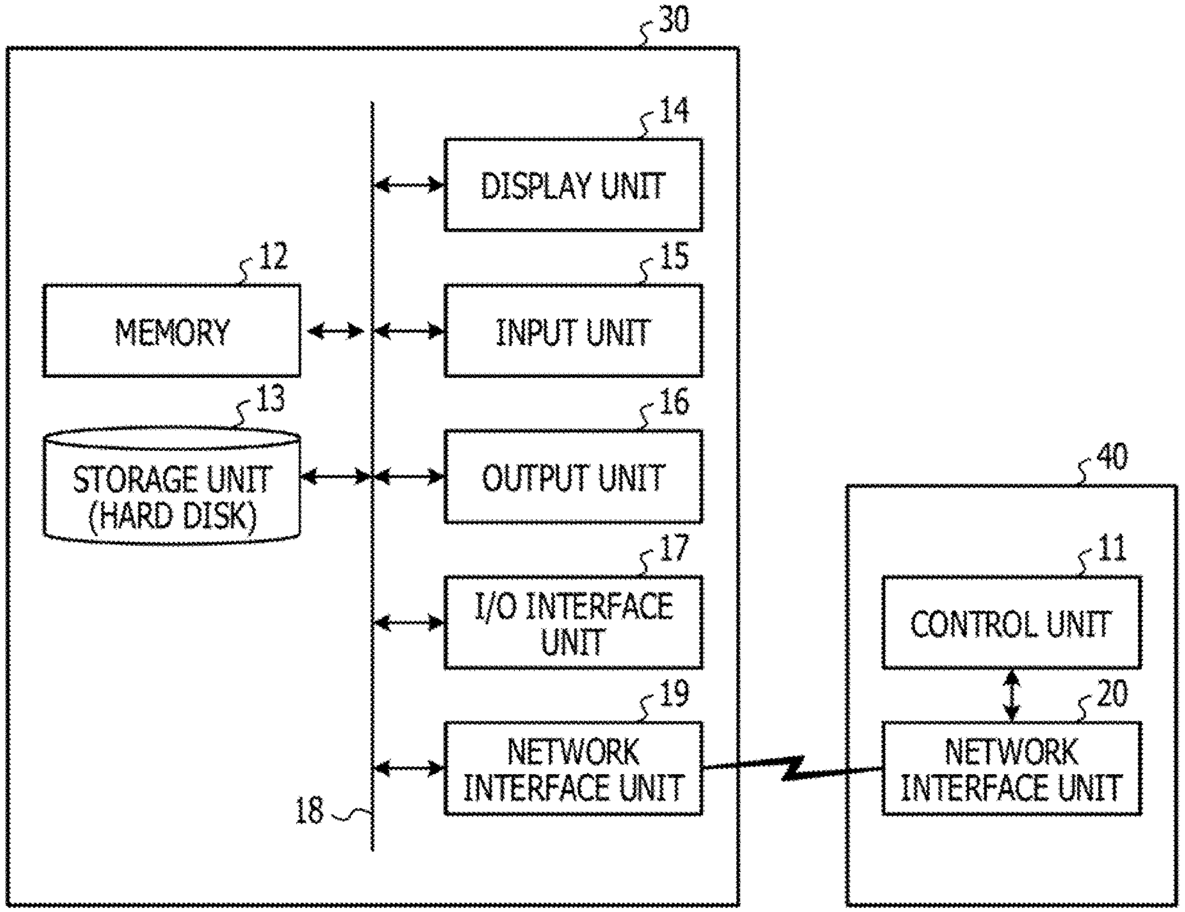
FIG. 12 is a diagram illustrating another configuration example of the material characteristic prediction apparatus disclosed herein.

FIG. 12 illustrates another hardware configuration example of the material characteristic prediction apparatus disclosed herein.

The example illustrated in FIG. 12 is an example when the material characteristic prediction apparatus is a cloud type, and the control unit 11 is independent from the storage unit 13 and the like. In the example illustrated in FIG. 13, a computer 30 in which the storage unit 13 and the like are included, and a computer 40 in which the control unit 11 is included are coupled via network interface units 19 and 20.

The network interface units 19 and 20 are hardware configured to perform communication by using the Internet.

Figure 13:
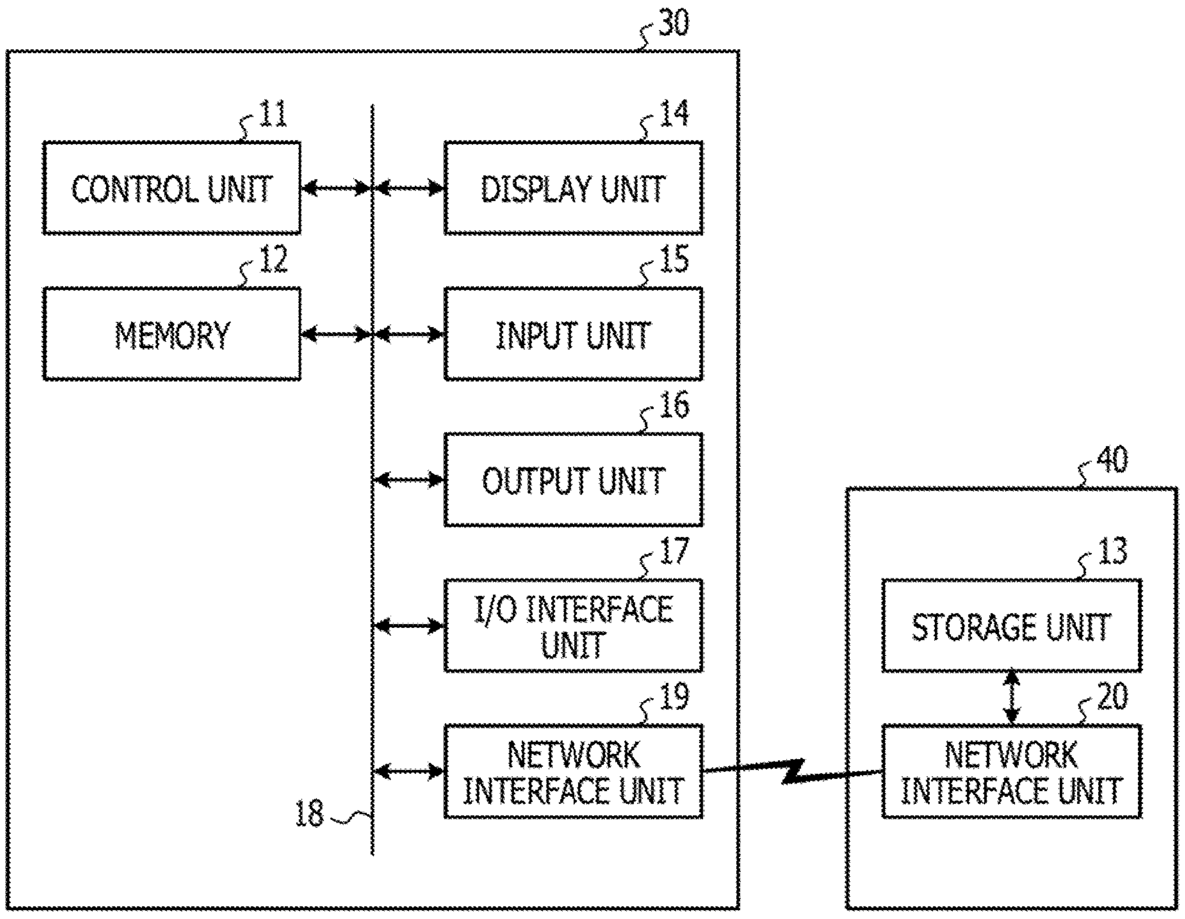
FIG. 13 is a diagram illustrating yet another configuration example of the material characteristic prediction apparatus disclosed herein.

FIG. 13 illustrates another hardware configuration example of the material characteristic prediction apparatus disclosed herein.

The example illustrated in FIG. 13 is an example when the material characteristic prediction apparatus is a cloud type, and the control unit 11 is independent from the storage unit 13 and the like. In the example illustrated in FIG. 13, the computer 30 in which the control unit 11 and the like are included, and the computer 40 in which the storage unit 13 is included are coupled via the network interface units 19 and 20.

Figure 14:
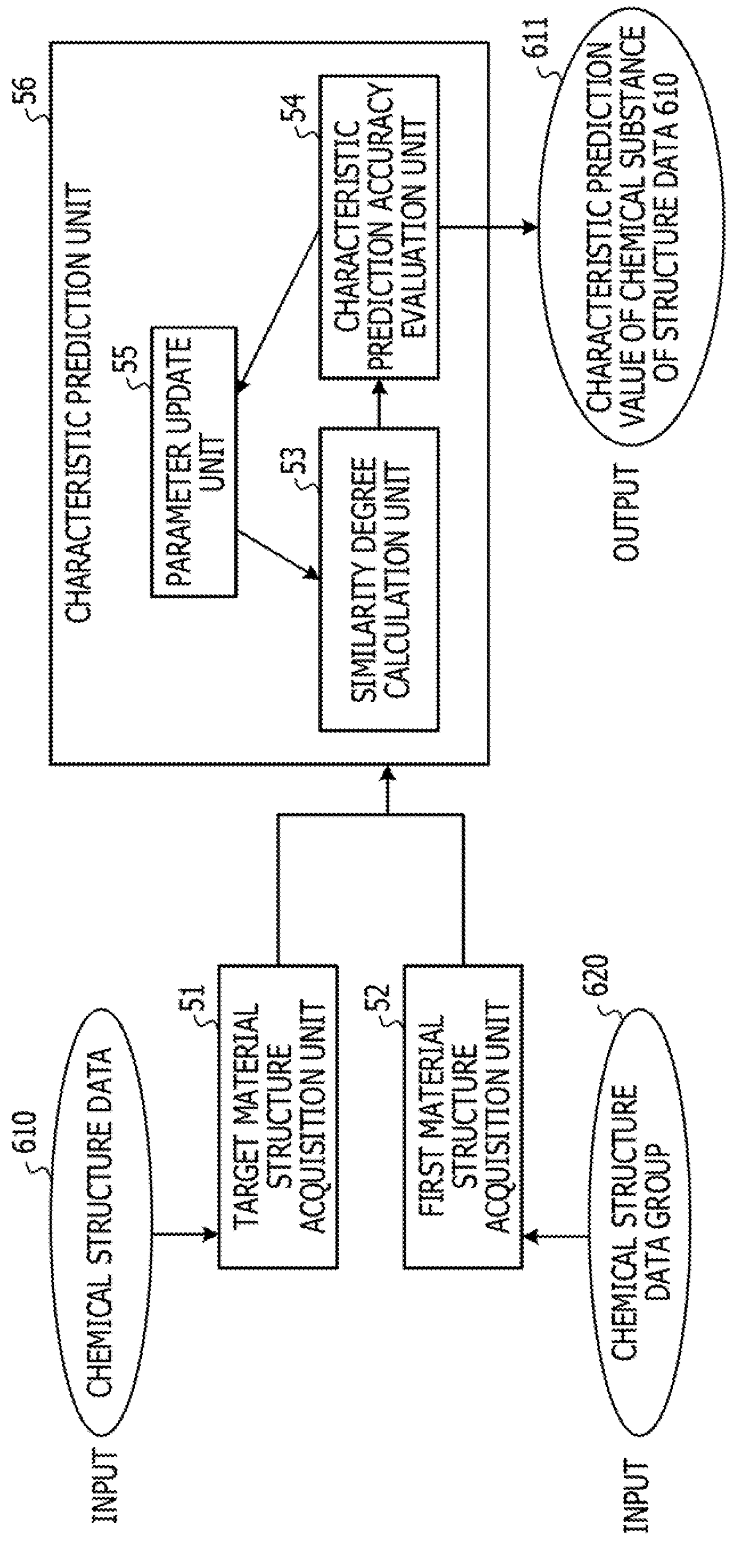
FIG. 14 is a diagram illustrating a functional configuration example as one embodiment of the material characteristic prediction apparatus disclosed herein.

FIG. 14 illustrates an example of a functional configuration of one embodiment of the material characteristic prediction apparatus disclosed herein.

As illustrated in FIG. 14, the material characteristic prediction apparatus 10 includes a target material structure acquisition unit 51, a first material structure acquisition unit 52, a similarity degree calculation unit 53, a characteristic prediction unit 56 including a characteristic prediction accuracy evaluation unit 54, and a parameter update unit 55.

The target material structure acquisition unit 51 reads chemical structure data 610 of a material (target material) whose characteristic value is unknown as input from a file format such as SDF.

The first material structure acquisition unit 52 reads a chemical structure data group 620 of a material group whose characteristic values are known as input from a file format such as SDF.

The similarity degree calculation unit 53 creates a conflict graph between the read chemical structure data 610 and each structure in the chemical structure data group 620, and minimizes the hamiltonian of formula (1) by annealing or the like, to search for a maximum independent set. The similarity degree calculation unit 53, based on the result, calculates a degree of similarity with the formula (2).

The characteristic prediction accuracy evaluation unit 54 calculates a correlation coefficient between the degree of similarity and a characteristic value according to a characteristic, and evaluates prediction accuracy.

The parameter update unit 55 updates the parameters in the above formula (1) such that the calculated prediction accuracy further increases (such that the correlation coefficient between the degree of similarity and the characteristic value according to a characteristic increases).

The material characteristic prediction apparatus 10 repeats the processing in the similarity degree calculation unit 53, the characteristic prediction accuracy evaluation unit 54, and the parameter update unit 55, and, when the correlation coefficient between the degree of similarity and the characteristic value according to the characteristic exceeds a threshold value, outputs a characteristic prediction value 611 of a target material of the chemical structure data 610.

Figure 15:
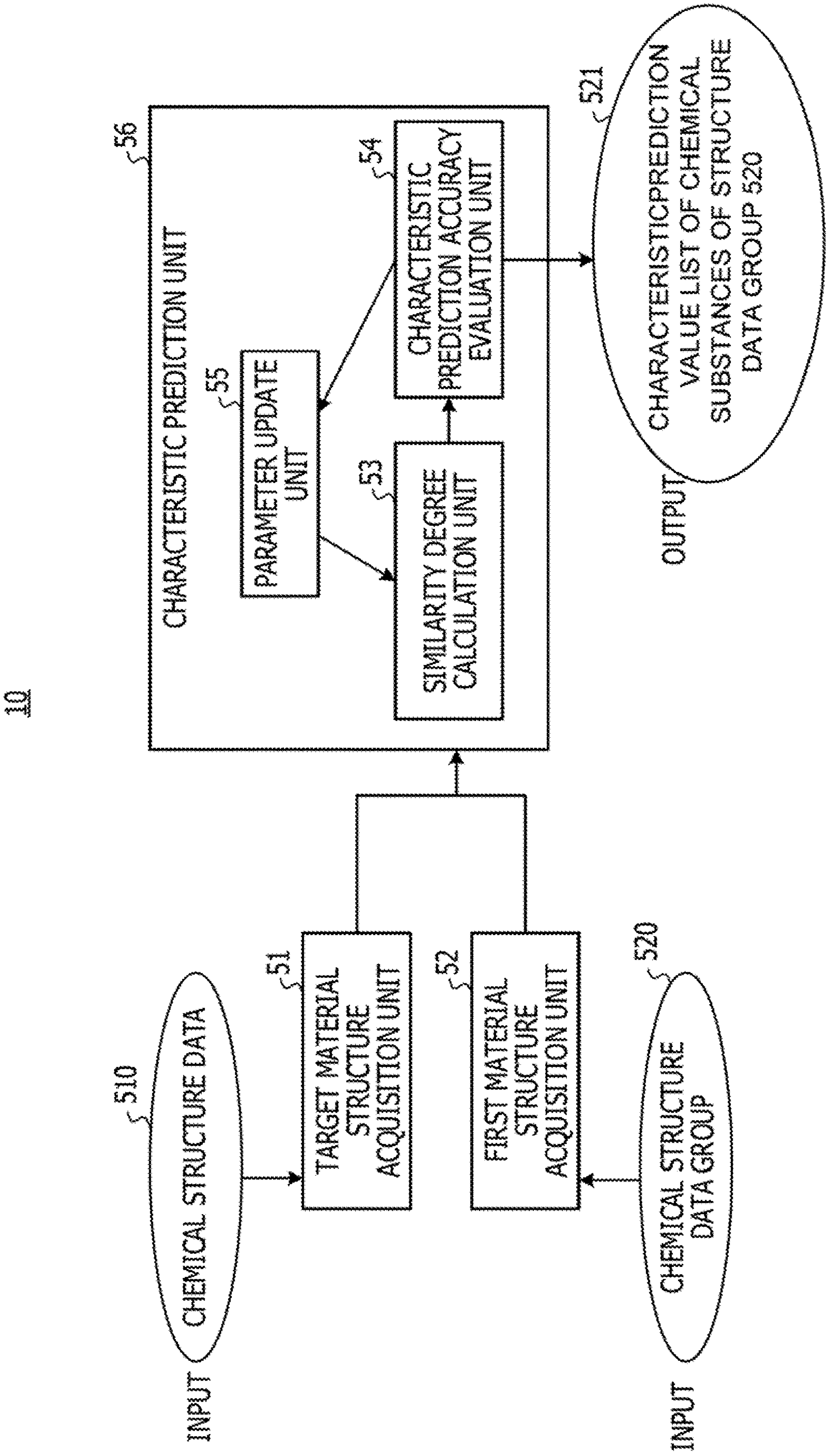
FIG. 15 is a diagram illustrating a functional configuration example as another embodiment of the material characteristic prediction apparatus disclosed herein.

As illustrated in FIG. 15, the target material structure acquisition unit 51 may also read a chemical structure data 510 of a material whose characteristic value is known from an SDF format file, and the first material structure acquisition unit 52 may read a chemical structure data group 520 of a material group whose characteristic values are unknown from an SDF format file. In this aspect, the material characteristic prediction apparatus 10 repeats the processing in the similarity degree calculation unit 53, the characteristic prediction accuracy evaluation unit 54, and the parameter update unit 55, and, when the correlation coefficient between the degree of similarity and the characteristic value according to the characteristic exceeds the threshold value, outputs a characteristic prediction value list 521 of the chemical structure data group 520.

Figure 16:
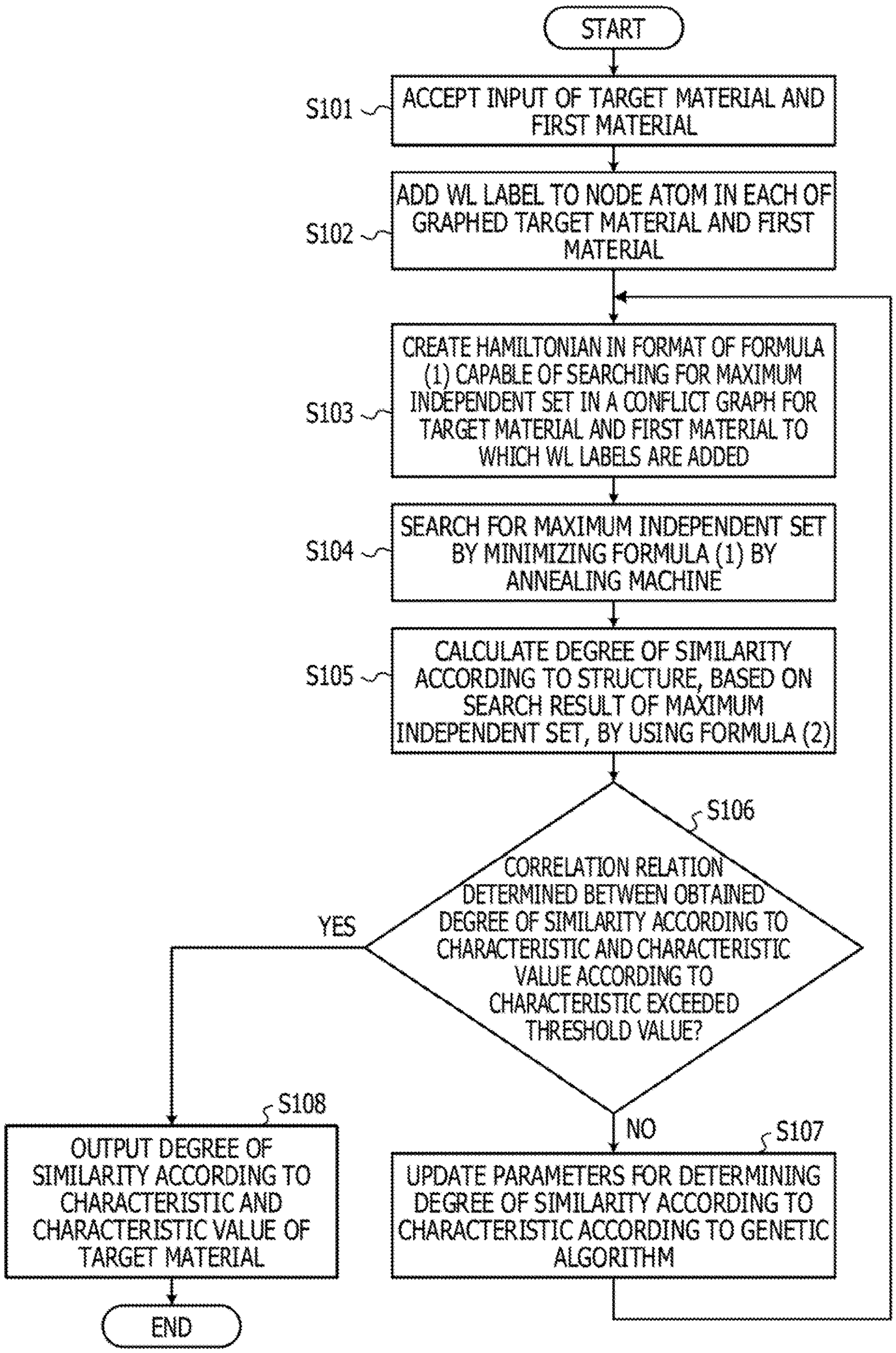
FIG. 16 is an example of a flowchart when one example of a technique disclosed herein is used for determining a degree of similarity according to a characteristic, to predict a characteristic value of a target material.

FIG. 16 illustrates an example of a flowchart when, one example of the technique disclosed herein is used to determine a degree of similarity according to a characteristic, thereby predicting a characteristic value of a target material.

First, the characteristic prediction unit 56 accepts input of a target material and a first material (S101). At this time, the characteristic prediction unit 56 may select a target material and a first material from a chemical structure data group (database) of target materials and first materials.

Next, the characteristic prediction unit 56 adds a WL label according to the Weisfeiler-Lehman procedure to a node atom in each of graphed target material and first material (S102), Subsequently, the characteristic prediction unit 56 creates a hamiltonian in the format of the above formula (1) capable of searching for a maximum independent set in a conflict graph for the target material and the first material to which WL labels are added (S103). For example, in S103, the characteristic prediction unit 56, based on information on the target material and the first material to which the WL labels are added, creates the above formula (1) that is a hamiltonian for which minimizing H means searching for a maximum independent set.

The characteristic prediction unit 56 searches for a maximum independent set by minimizing the above formula (1) by an annealing machine (S104). For example, in S103, the characteristic prediction unit 56 performs a ground state search using an annealing method for the above formula (1), to calculate minimum energy in the above formula (1), thereby searching for a maximum independent set.

The annealing machine is not particularly limited as long as it is a computer employing an annealing method for performing the ground state search on an energy function represented by the Ising model, and may be appropriately selected according to the purpose. Examples of the annealing machine include a quantum annealing machine, a semiconductor annealing machine using a semiconductor technology, and a machine for performing simulated annealing performed by software using a CPU or a graphics processing unit (GPU). As an annealing machine, for example, Digital Annealer (registered trademark) may be used.

Next, the characteristic prediction unit 56, based on a search result of a maximum independent set found in S104, uses the above formula (2) to calculate a degree of similarity according to a characteristic (S105).

Subsequently, the characteristic prediction unit 56 determines whether a correlation coefficient determined between a degree of similarity according to a characteristic and a characteristic value according to the characteristic exceeds a threshold value or not (S106). When determining that the correlation coefficient determined between the degree of similarity according to the characteristic and the characteristic value according to the characteristic is equal to or less than the threshold value, the characteristic prediction unit 56 advances the processing to S107. On the other hand, when determining that the correlation coefficient determined between the degree of similarity according to the characteristic and the characteristic value according to the characteristic exceeds the threshold value, the characteristic prediction unit 56 advances the processing to S108.

In S107, the characteristic prediction unit 56 updates parameters for determining the degree of similarity according to the characteristic, according to a genetic algorithm, such that the correlation coefficient between the degree of similarity according to the characteristic and the characteristic value according to the characteristic increases. As the parameter to be updated, at least one of the parameters i) to iv, and the formula itself of the similarity degree evaluation formula S of v) described above may be selected.

The characteristic prediction unit 56, when the parameters are updated in S107, returns the processing to S103.

In S108, the characteristic prediction unit 56 outputs the degree of similarity according to the characteristic, and a predicted characteristic of a target material. A format for outputting a result is not particularly limited, and may be appropriately selected according to a purpose.

Figure 17A:
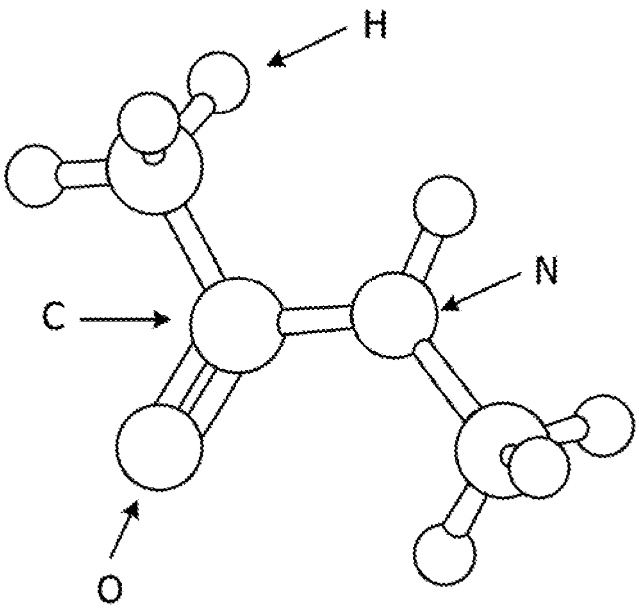
FIG. 17A is a diagram illustrating one example of a molecular structure of N-methylacetamide.
Figure 17B:
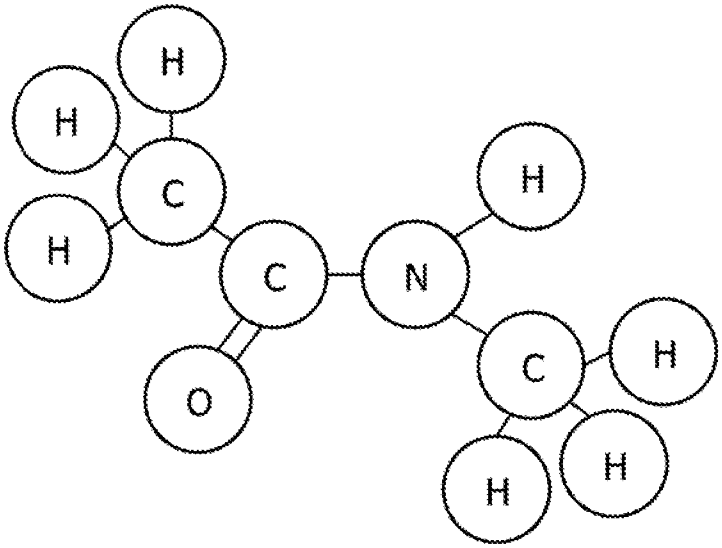
FIG. 17B is a diagram illustrating an example when the molecular structure illustrated in FIG. 17A is graphed, in which a label of a node atom is a type (element) of the atom.
Figure 17C:
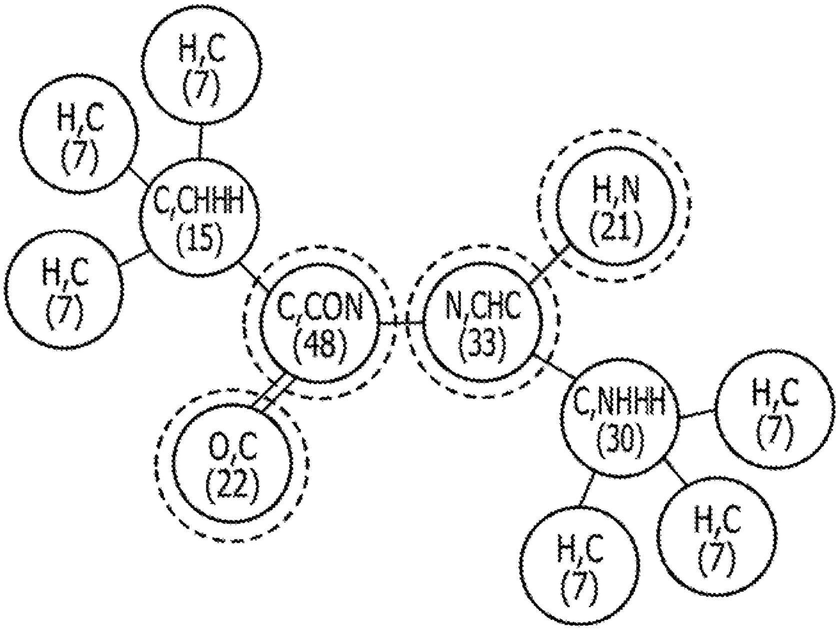
FIG. 17C is a diagram illustrating an example of a molecular structure of N-methylacetamide to which a WL label in one example of the technique disclosed herein is added.

FIGS. 17A to 17C illustrate, by using N-methylacetamide as an example, a molecular structure, a graphed molecular structure, and a molecular structure to which WI labels are added in one example of the technique disclosed herein, respectively.

FIG. 17A illustrates one example of the molecular structure of N-methylacetamide. FIG. 17B illustrates a diagram obtained by graphing the molecular structure illustrated in FIG. 17A, in which a label of a node atom is a type (element) of the atom.

In the molecular structure illustrated in FIG. 17C to which the WL labels in the one example of the technique disclosed herein are added, the WL labels including label information of nearest nodes (directly coupled nodes), such as [H, C], [C, CHHH], [C, CON], [O, C], [N, CHC], and [H, N] are added. For example, in this example, a WL label is added to a node atom by performing the Weisfeiler-Lehman procedure once.

In the example illustrated in FIG. 17C, a number in ( ) is a numerical value representing one example of an evaluation index $B_i$ at each node atom. In this example, a contribution value ΔB of each element is set such that ΔB(H)=1, ΔB(C)=6, ΔB(O)=16, and ΔB(N)=20, and an evaluation index B at each node atom is set to a sum of the contribution values ΔB of the node atom. The contribution value ΔB of each element may be appropriately selected based on an element included in a material, and for example, when sulfur (S) is contained in a target material or a first material, AB(S) may be added as one of the contribution values ΔB.

Figure 18:
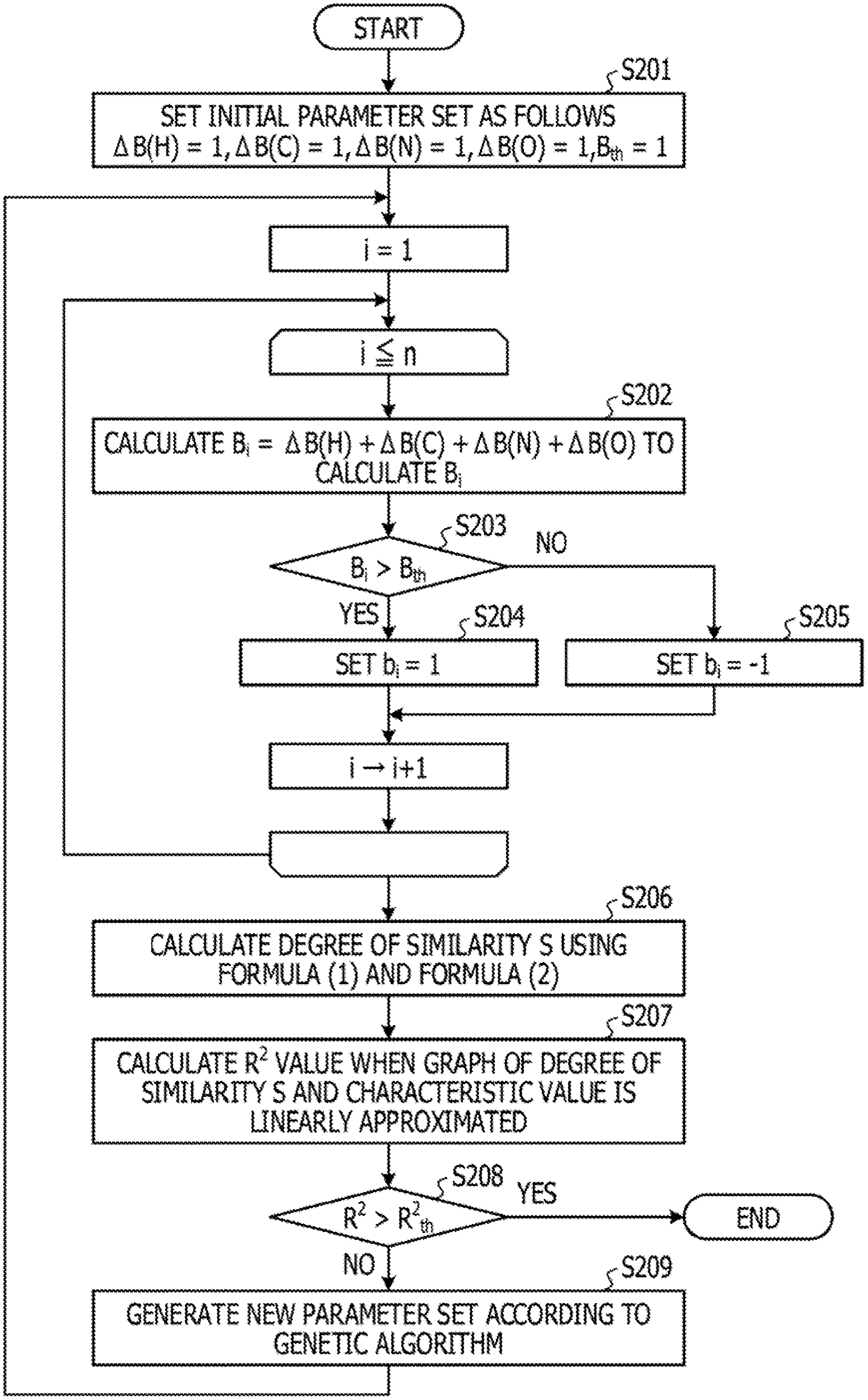
FIG. 18 is an example of a flowchart when one example of the technique disclosed herein is used to update parameters for determining a degree of similarity according to a characteristic.

FIG. 18 illustrates an example of a flowchart when using the one example of the technique disclosed herein, to update parameters for determining a degree of similarity according to a characteristic. With reference to FIG. 18, a method will be described, in which, in order to increase a correlation coefficient between a degree of similarity according to a characteristic and a characteristic value according to the characteristic, a contribution value ΔB of each element for an evaluation index $B_i$ in each node atom, and a threshold value $B_{th}$ of an evaluation index $B_i$ are optimized.

First, the characteristic prediction unit 56 sets initial parameter values such that, ΔB(H)=1, ΔB(C)=1, ΔB(O)=1, ΔB(N)=1, and $B_{th}$=1 (S201).

Next, the characteristic prediction unit 56, for each node atom, based on a formula of an evaluation index $B_i$=ΔB(H)+ΔB(C)+ΔB(G)+ΔB(N), calculates an evaluation index $B_i$ (S202).

Subsequently, the characteristic prediction unit 56 determines whether an evaluation index $B_i$ of a node atom constituting an i-th node exceeds a threshold value $B_{th}$ or not (S203). In S203, when determining that the evaluation index $B_i$ in the i-th node exceeds the threshold value $B_{th}$, the characteristic prediction unit 56 advances the processing to S204. On the other hand, when determining that the evaluation index $B_i$ in the i-th node is equal to or less than the threshold value $B_{th}$, the characteristic prediction unit 56 advances the processing to S205.

In S204, the characteristic prediction unit 56 sets $b_i$ in the above formula (1) to 1. As described above, setting $b_i$ to 1 corresponds to searching for a maximum independent set such that the i-th node is included in the above formula (1).

In S205, the characteristic prediction unit 56 sets $b_i$ in the above formula (1) to −1. As described above, setting $b_i$ to −1 corresponds to searching for a maximum independent set such that the i-th node is excluded in the above formula (1).

After the processing from S202 to S205 is performed for all node atoms, the characteristic prediction unit 56 uses the above formulas (1) and (2) to calculate a degree of similarity according to a characteristic (S206).

Minimization of the above formula (1) (search for a maximum independent set) is performed, for example, by using an annealing machine.

Subsequently, in S207, the characteristic prediction unit 56 calculates an $R^2$ value (correlation coefficient) when a graph obtained by plotting degrees of similarity according to a characteristic and characteristic values according to the characteristic is linearly approximated.

Next, the characteristic prediction unit 56 determines whether the calculated $R^2$ value exceeds a threshold value ($R^2_{th}$) of the correlation coefficient or not (S208). In S208, when determining that the calculated $R^2$ value is equal to or less than $R^2_{th}$, the characteristic prediction unit 56 advances the processing to S209. In S208, when determining that the calculated $R^2$ value exceeds $R^2_{th}$, the characteristic prediction unit 56 regards that the parameters are optimized, and ends the processing.

In S209, according to the genetic algorithm, after updating the respective numerical values of ΔB(H), ΔB(C), ΔB(O), ΔB(N), and $B_{th}$, the characteristic prediction unit 56 returns the processing to S202, and performs the processing from S202 to S205 for each node atom once again.

In this manner, by repeating the parameter update until the correlation coefficient between the degree of similarity according to the characteristic and the characteristic value according to the characteristic exceeds the threshold value of the correlation coefficient, it is possible to optimize the parameters for calculating the degree of similarity according to the characteristic, thereby predicting a characteristic value of a target material with higher accuracy.

Figure 19:
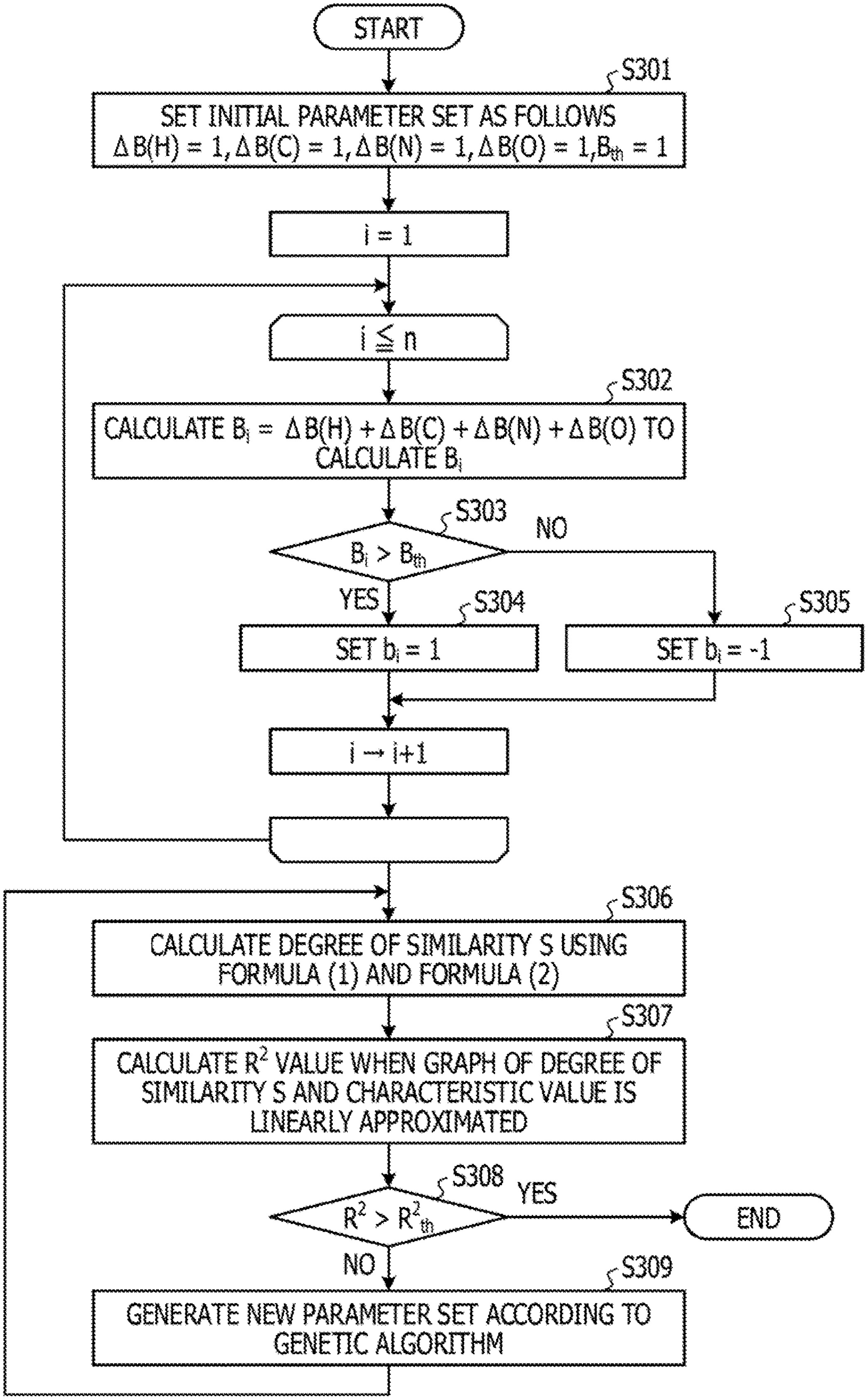
FIG. 19 is another example of the flowchart when the one example of the technique disclosed herein is used to update parameters for determining a degree of similarity according to a characteristic.

FIG. 19 illustrates another example of a flowchart when the one example of the technique disclosed herein is used to update parameters for determining a degree of similarity according to a characteristic. Processing in S301 to S308 in FIG. 19 is similar to that in S201 to S208 in FIG. 18, thus description thereof will be omitted.

In S309, according to a genetic algorithm, after updating at least one of a numerical value of $w_{ij}$ in the above formula (1), and a similarity degree evaluation formula S represented by the above formula (2), the characteristic prediction unit 56 returns the processing to S306. In this manner, the one example of the technique disclosed herein may be an aspect in which the parameters of the above formulas (1) and (2) are updated.

One example of an annealing method and an annealing machine will be described below.

The annealing method is a method of obtaining a solution stochastically by using a random number value or a superposition of quantum bits. Hereinafter, a problem of minimizing a value of an evaluation function to be optimized will be described as an example, and the value of the evaluation function will be referred to as energy. When the value of the evaluation function is maximized, a sign of the evaluation function may be changed.

First, starting with an initial state in which one discrete value is assigned to an individual variable, from the current state (a combination of values of variables), a state close to the current state (for example, a state in which only one of the variables has been changed) is selected, and the state transition is examined. A change in energy associated with the state transition is calculated, and it is stochastically determined whether to adopt the state transition and change the current state or to maintain the original state without adopting the state transition, according to the calculated value. When setting an adoption probability of a state transition that results in a drop in the energy to be greater than that of a state transition that results in a rise in the energy, state changes occur in a direction in which the energy drops on average, and thus it is possible to expect that the state is transitioned to a more suitable state with the lapse of time. Therefore, an approximate solution that possibly results in energy close to the optimal solution or optimal value may be finally obtained.

When a state transition that results in a drop in the energy in a deterministic way is adopted and a state transition that results in a rise in the energy is not adopted, the change in energy broadly monotonically decreases over time, however, once a local solution is reached, no further change may occur. Since an extraordinarily large number of local solutions exist in a discrete optimization problem as described above, the state is stuck at a local solution that is not very close to an optimal value, in many cases. Therefore, in solving a discrete optimization problem, it is important to determine whether or not to adopt the state stochastically.

In the annealing method, it has been proved that the state reaches the optimal solution at a limit of infinite time (the number of iterations) as long as the adoption (acceptance) probability of the state transition is determined as follows.

Hereinafter, a method for determining an optimal solution using an annealing method will be described in order.

(3) For an energy change (energy decrease) value ($-\Delta E$) associated with a state transition, an acceptance probability p of the state transition is determined by any of the following functions f( ).

$$p(\Delta E,t)=F(-\Delta E/T) \quad (3\text{-}1)$$

$$f_{metro}(x)=\min(1,e^x) \quad \text{(Metropolis Method)} \quad (3\text{-}2)$$

$$f_{Gibbs}(x)=\frac{1}{1+e^{-x}} \quad \text{(Gibbs Method)} \quad (3\text{-}3)$$

T is a parameter lied a temperature value, and for example, may be changed as follows.

(4) A temperature value T is logarithmically reduced with respect to the number of iterations t as represented by the following formula.

$$T=\frac{T_0\log(c)}{\log(t+c)} \quad (4)$$

$T_0$ represents an initial temperature value and it is desirable that a sufficiently large value be set in accordance with the problem.

In a case of using the acceptance probability expressed by form a (3), when a steady state is reached after sufficient number of iterations, an occupation probability of an individual state is in accordance with a Boltzmann distribution at thermal equilibrium state in thermodynamics.

Since the occupation probability of a lower-energy state increases when the temperature gradually decreases from high initial temperature, a low-energy state is supposed to be obtained when the temperature sufficiently decreases. This method is referred to as an annealing method (or pseudo-annealing method) because this behavior resembles state change when annealing a material. Stochastic occurrence of a state transition that results in a rise in the energy corresponds to thermal excitation in physics.

Figure 20:
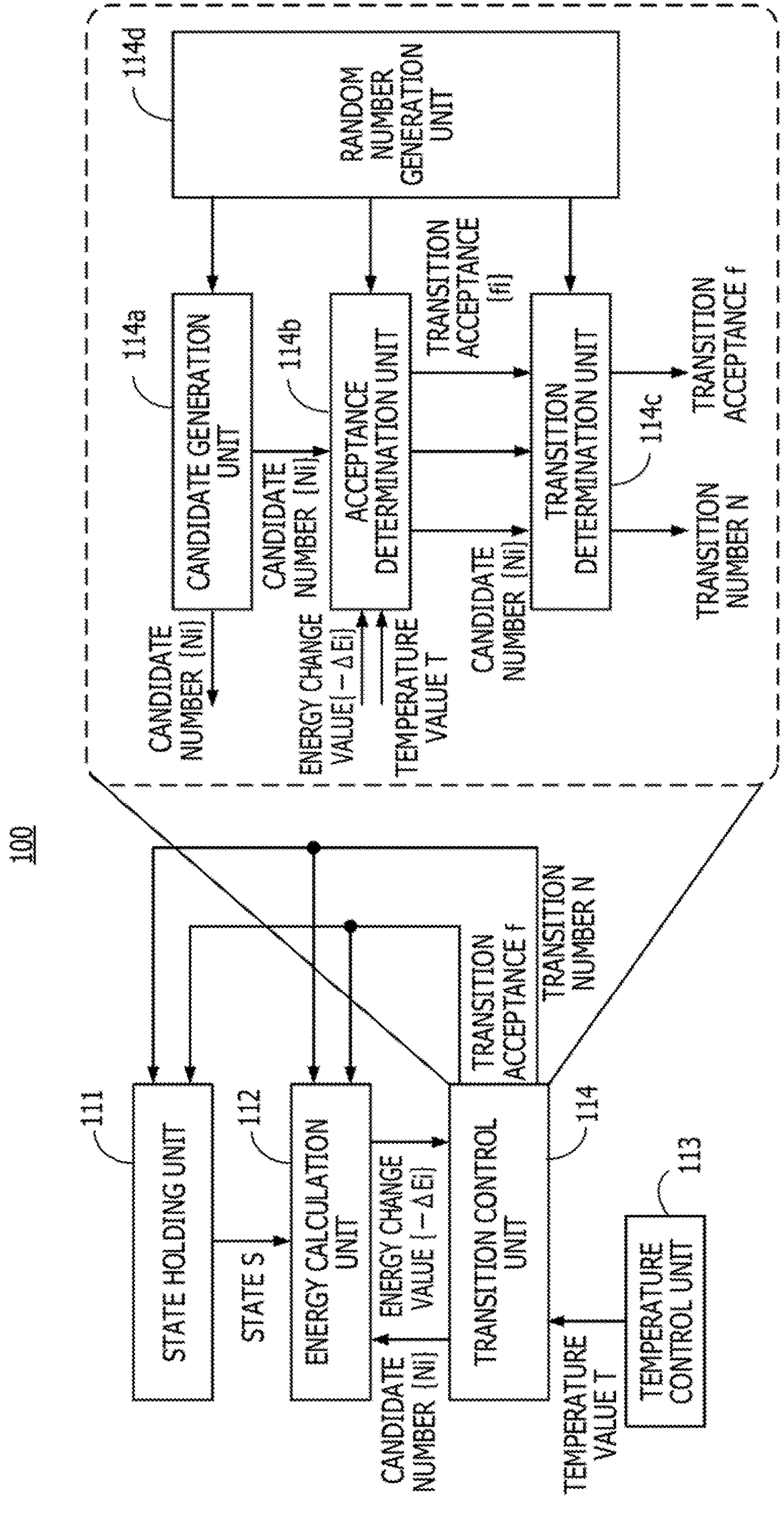
FIG. 20 is a diagram illustrating an example of a functional configuration of an optimization apparatus (control unit) used in an annealing method.

FIG. 20 illustrates one example of a functional configuration of an optimization apparatus (control unit 11) for performing the annealing method. While, cases where a plurality of candidates for the state transition is generated will be also described in the following description, the transition candidates are generated one by one in the basic annealing method.

Δn optimization apparatus 100 includes a state holding unit 111 configured to hold a current state S (values of a plurality of state variables). The optimization apparatus 100 also includes an energy calculation unit 112 configured to calculate energy change values $\{-\Delta Ei\}$ of state transitions in a case where the state transition occurs from the current state S as a result of change in any of the values of the plurality of state variables. The optimization apparatus 100 includes a temperature control unit 113 configured to control the temperature value T and a transition control unit 114 configured to control state changes.

The transition control unit 114 stochastically determines whether or not any one of a plurality of state transitions is accepted, depending on a relative relationship between the energy change values $\{-\Delta Ei\}$ and thermal excitation energy based on the temperature value T, the energy change values $\{-\Delta Ei\}$, and the random number value.

The transition control unit 114 includes a candidate generation unit 114*a* for generating a candidate for a state transition, and an acceptance determination unit 114*b* for stochastically determining whether or not the state transition is accepted from the energy change values $\{-\Delta Ei\}$ of the candidates and the temperature value T for each candidate. The transition control unit 114 includes a transition determination unit 114*c* for determining a candidate to be adopted from the accepted candidates, and a random number generation unit 114*d* for generating a probability variable.

The operation in one iteration in the optimization apparatus 100 is as follows.

First, the candidate generation unit 114*a* generates one or a plurality of candidates (candidate numbers $\{Ni\}$) for the state transition from the current state S held by the state holding unit 111 to the next state. The energy calculation unit 112 calculates energy change values $\{-\Delta Ei\}$ for each of the state transitions for the candidates, by using the current state S and the candidates for the state transition. The acceptance determination unit 114*b* uses the temperature value T generated in the temperature control unit 113 and a probability variable (random number value) generated by the random number generation unit 114*d*, and accepts the state transition with the acceptance probability expressed by the above formula (3) according to the energy change values $\{-\Delta Ei\}$ of the respective state transitions.

The acceptance determination unit 114*b* outputs the acceptances $\{fi\}$ of the respective state transitions. In a case where a plurality of state transitions is accepted, the transition determination unit 114*c* randomly selects one thereof by using a random number value. The transition determination unit 114*c* then outputs a transition number N of the selected state transition, and a transition acceptance f. In a case where there is an accepted state transition, the values of the state variable stored in the state holding unit 111 is updated according to the adopted state transition.

Starting with the initial state, the above-described iteration processes are repeated while causing the temperature control unit 113 to lower the temperature value, and the operation ends when a certain number of iterations is reached, or when an end determination condition, for example, the energy becomes lower than a predetermined value, is satisfied. The solution outputted by the optimization apparatus 100 is the state corresponding to the end of the operation.

Figure 21:
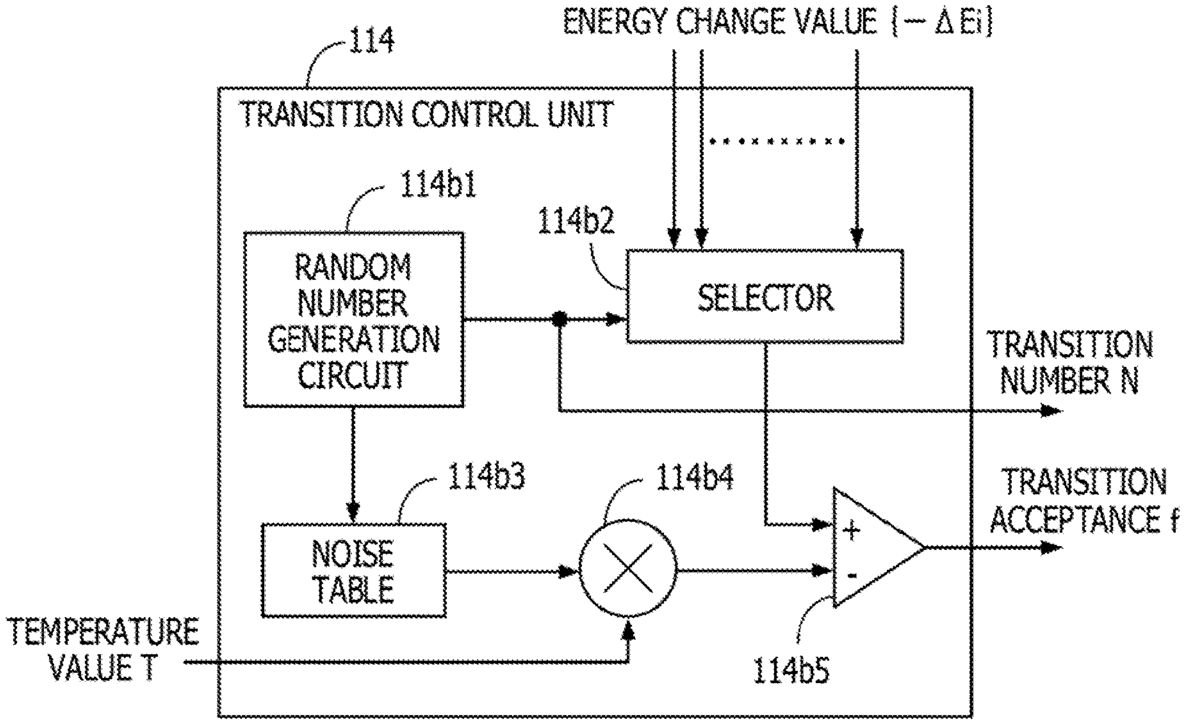
FIG. 21 is a block diagram illustrating an example of a circuit level of a transition control unit.

FIG. 21 is a block diagram of a transition control unit in a normal annealing method for generating candidates one by one, for example, a block diagram of a circuit level of a configuration example of an arithmetic portion demanded for the acceptance determination unit.

The transition control unit 114 includes a random number generation circuit **114*b*1, a selector 114*b*2, a noise table 114*b*3, a multiplier 114*b*4, and a comparator 114*b*5**.

Of all the energy change values {−ΔEi} calculated for the candidates of the respective state transitions, the selector **114*b*2 selects and outputs an energy change value corresponding to the transition number N, which is a random number value generated by the random number generation circuit 114*b*1**.

Functions of the noise table **114*b*3 will be described later. As the noise table 114*b*3**, for example, a memory such as a RAM, a flash memory, or the like may be used.

The multiplier **114*b*4 outputs a product obtained by multiplying a value outputted by the noise table 114*b*3** by the temperature value T (corresponding to the thermal excitation energy described above).

The comparator **114*b*5 outputs a comparison result in which the multiplication result outputted by the multiplier 114*b*4 is compared with the energy change value −ΔE that is the energy change value selected by the selector 114*b*2**, as the transition acceptance f.

Although the transition control unit 114 illustrated in FIG. 21 basically implements the functions described above without change, a mechanism of accepting a state transition with the acceptance probability expressed by formula (3) will be described in more detail.

A circuit that outputs 1 when the acceptance probability p is established and outputs 0 when the acceptance probability (1−p) is established may be realized by a comparator that has two inputs A and B, outputs 1 when A>B, and outputs 0 when A<B by inputting the acceptance probability p to the input A and a uniform random number having a value in a section [0, 1) to the input B. Thus, with an input of the value of the acceptance probability p calculated by using formula (3) based on the energy change value and the temperature value T to the input A of the comparator, it is possible to realize the above function.

For example, assuming that f is the function used in formula (3), and that u is a uniform random number having a value in the section [0, 1), the circuit that outputs 1 when f(ΔE/T) is greater than u realizes the above function.

The same function as that described above may be realized by any of the following variations.

Even when the same monotonically increasing function is applied to two numbers, the two numbers maintain the same magnitude relationship. Therefore, even when the same monotonically increasing function is applied to the two inputs of the comparator, the same output is obtained. When an inverse function $f^{-1}$ of f is adopted as this monotonically increasing function, it is seen that a circuit that outputs 1 when −ΔE/T is greater than $f^{-1}(u)$ may be adopted. Since the temperature value T is positive, it is seen that a circuit that outputs 1 when −ΔF is greater than $Tf^{-1}(u)$ is suitable.

The noise table **114*b*3 in FIG. 21** is a conversion table for realizing the inverse function $f^{-1}(u)$, and is a table for outputting a value of the next function with respect to the input obtained by discretizing the section [0, 1).

$$f_{metro}^{-}(u)=\log(u) \quad (5\text{-}1)$$

$$f_{Gibbs}^{-1}(u)=\log\left(\frac{u}{1-u}\right) \quad (5\text{-}2)$$

Although the transition control unit 114 includes a latch that holds a determination result and the like, a state machine that generates the corresponding timing, and the like, these components are not illustrated in FIG. 21 for simple illustration.

Figure 22:
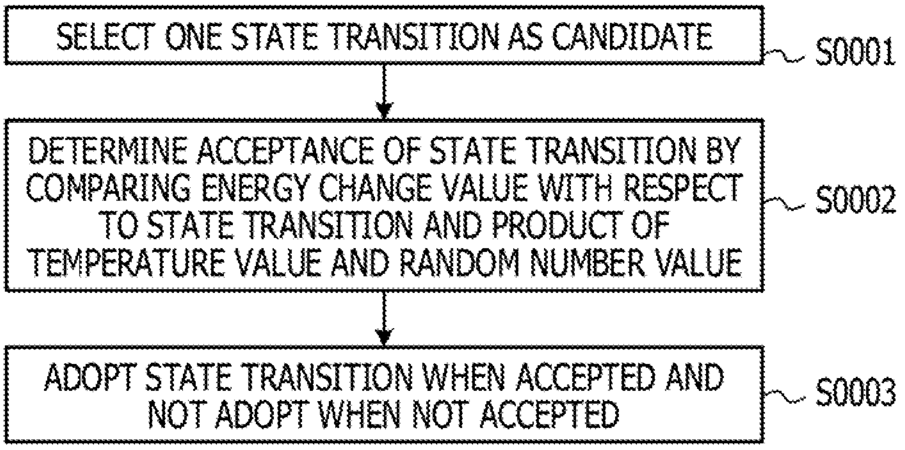
FIG. 22 is a diagram illustrating an example of an operation flow of the transition control unit.

FIG. 22 is a diagram illustrating one example of an operation flow of the transition control unit 114. The operation flow illustrated in FIG. 22 includes a step of selecting one state transition as a candidate (S0001), a step of determining whether a state transition is accepted or not by comparing the energy change value with respect to the state transition with a product of a temperature value and a random number value (S0002), and a step (S0003) in which the state transition is adopted when the state transition is accepted, and the state transition is not adopted when the state transition is not accepted.

Material Characteristic Prediction Method

A material characteristic prediction method disclosed herein is a material characteristic prediction method for predicting a characteristic value of a characteristic of a target material, and includes a characteristic prediction process for determining a degree of similarity according to a characteristic between a target material and a first material whose characteristic value is a first value, to predict a characteristic value of the target material.

The material characteristic prediction method disclosed herein may be performed by, for example, the material characteristic prediction apparatus disclosed herein. A preferred aspect in the material characteristic prediction method disclosed herein may be similar to the preferred aspect in the material characteristic prediction apparatus disclosed herein.

Material Characteristic Prediction Program

A material characteristic prediction program disclosed herein is a material characteristic prediction program for predicting a characteristic value of a characteristic of a target material, and causes a computer to perform characteristic prediction processing, in which a degree of similarity according to a characteristic between a target material and a first material whose characteristic value of a characteristic is a first value is determined, to predict a characteristic value of the target material.

The material characteristic prediction program disclosed herein may be, for example, a program that causes a computer to execute the material characteristic prediction method disclosed herein, A preferred aspect in the material characteristic prediction program disclosed herein may be, for example, similar to the preferred aspect in the material characteristic prediction apparatus disclosed herein.

The material characteristic prediction program disclosed herein may be created using any of various known program languages according to a configuration of a computer system to be used, and a type, a version, and the like of an operating system.

The material characteristic prediction program disclosed herein may be recorded on a recording medium such as a built-in hard disk, an external hard disk, or the like, or recorded on a recording medium such as a CD-ROM, a DVD-ROM, an MO disk, or a USB memory. The material characteristic prediction program may be constituted by one or two or more programs, and may be stored in a plurality of recording media.

In a case where the material characteristic prediction program disclosed herein is recorded on the recording medium described above, the material characteristic prediction program is directly used, or used by installing the material characteristic prediction program on a hard disk, through a recording medium reading apparatus included in the computer system, as appropriate. The material characteristic prediction program disclosed herein may be recorded in an external storage area (another computer or the like) accessible from the computer system through an information communication network. In this case, the material characteristic prediction program disclosed herein, which is recorded in the external storage area may be directly used or be used by installing the material characteristic prediction program on the hard disk from the external storage area through the information communication network, as appropriate.

The material characteristic prediction program disclosed herein nay be divided and recorded on a plurality of recording media for each arbitrary process.

Computer Readable Recording Medium

The computer readable recording medium disclosed herein is configured to record the material characteristic prediction program disclosed herein.

The computer readable recording medium disclosed herein is not particularly limited, and may be appropriately selected according to the purpose, and examples thereof include, for example, a built-in hard disk, an external hard disk, a CD-ROM, a DVD-ROM, an MO disk, a USB memory, and the like.

The computer readable recording medium disclosed herein may be a plurality of recording media in which the material characteristic prediction program disclosed herein is divided and recorded for each arbitrary process.

Calculation Example

As one calculation example of the material characteristic prediction apparatus disclosed herein, an example will be described, according to the flows illustrated in FIGS. 16 and 18, in which a contribution value ΔB of each element and a threshold value $B_{th}$ of an evaluation index $B_i$ are optimized, and a degree of similarity according to a relative permittivity as a characteristic is calculated.

In this calculation example, as illustrated in FIG. 18, initial parameter values are set such that ΔB(H)=1, ΔB(C)=1, ΔB(O)=1, ΔB(N)=1, and $B_{th}$=1, and a threshold value of a correlation coefficient ($R^2_{th}$) is set to 0.7.

For each of seven materials illustrated in Table 1 below, a degree of similarity was calculated using N-methylacetamide of No. 0 as a query material.

TABLE 1

| No. | PubChem CID | COMPOUND NAME | CHEMICAL FORMULA (STRUCTURAL FORMULA) | RELATIVE PERMITTIVITY |
|---|---|---|---|---|
| 0 | 6582 | N-methyacetamide | CH3CONHCH3 | 191.3 |
| 1 | 31254 | N-methylformamide | HCONHCH3 | 182.4 |
| 2 | 713 | Formamide | HCONH2 | 111 |
| 3 | 31374 | N,N-dimethylacetamide | CH3CON(CH3)2 | 37.78 |
| 4 | 6228 | N,N-dimethylformamide | HCON(CH3)2 | 36.71 |
| 5 | 13387 | N-methyl-2-pyrrolidone | CH2CH2CH2CONCH3 | 32.2 |
| 6 | 8857 | Ethyl acetate | CH3COOC2H5 | 6.02 |

With respect to the materials illustrated in Table 1, the contribution value ΔB of each element and the threshold value $B_{th}$ of the evaluation index $B_i$ were optimized according to the flows illustrated in FIGS. 16 and 18, and the parameters when the threshold value ($R^2_{th}$) of the correlation coefficient exceeded 0.7 were as follows. ΔB(H)=1, ΔB(C)=6, AB(O)=16, ΔB(N)=20, and $B_{th}$=20

A degree of similarity S1 according to a characteristic (relative permittivity) calculated according to the above formulas (1) and (2) using the parameters described above is illustrated in Table 2.

For comparison, a degree of similarity S0 is determined, based only on structure of a material, by using the related art described in Non-Patent Document 1. The result is illustrated in Table 2.

TABLE 2

| No. | COMPOUND NAME | CHEMICAL FORMULA (STRUCTURAL FORMULA) | RELATIVE PERMITTIVITY | DEGREE OF SIMILARITY S0 | DEGREE OF SIMILARITY S1 |
|---|---|---|---|---|---|
| 0 | N-methylacetamide | CH3CONHCH3 | 191.3 | 1 | 1 |
| 1 | N-methylformamide | HCONHCH3 | 182.4 | 0.777777778 | 0.8 |
| 2 | Formamide | HCONH2 | 111 | 0.5 | 0.4 |
| 3 | N,N-dimethylacetamide | CH3CON(CH3)2 | 37.78 | 0.825 | 0.6 |
| 4 | N,N-dimethylformamide | HCON(CH3)2 | 36.71 | 0.833333333 | 0.4 |

TABLE 2-continued

| No. | COMPOUND NAME | CHEMICAL FORMULA (STRUCTURAL FORMULA) | RELATIVE PERMITTIVITY | DEGREE OF SIMILARITY S0 | DEGREE OF SIMILARITY S1 |
|---|---|---|---|---|---|
| 5 | N-methyl-2-pyrrolidone | CH2CH2CH2CONCH3 | 32.2 | 0.729166667 | 0.3429 |
| 6 | Ethyl acetate | CH3COOC2H5 | 6.02 | 0.851190476 | 0.225 |

Figure 23:
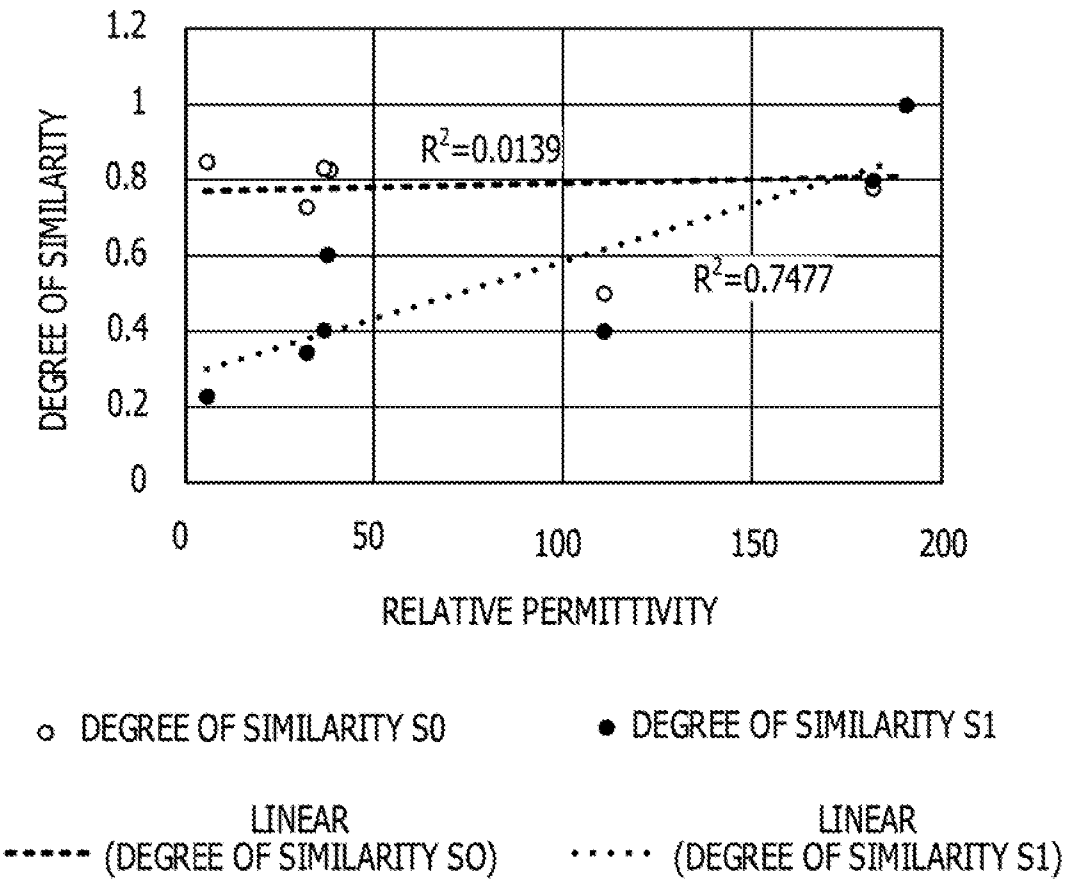
FIG. 23 is a diagram illustrating an example of a graph obtained, based on a result illustrated in Table 2, by plotting degrees of similarity and characteristic values (relative permittivity) according to a characteristic, and drawing an approximate straight line obtained by linearly approximating the plots.

Based on the result illustrated in Table 2, one example of a graph obtained by plotting the degrees of similarity and characteristic values (relative permittivities) according to a characteristic, and drawing an approximate straight line obtained by linearly approximating these plots is illustrated in FIG. 23.

As illustrated in FIG. 23, the correlation coefficient between the degree of similarity S1 calculated using one embodiment of the technique disclosed herein and a relative permittivity was 0.7477. On the other hand, the correlation coefficient between the degree of similarity S0 determined using the related art and a relative permittivity was 0.0139.

From this, it is found that, in the one embodiment of the technique disclosed herein, by optimizing the contribution value ΔB of each element and the threshold value $B_{th}$ of the evaluation index the degree of similarity according to the characteristic may be obtained.

When the approximate straight line of the degree of similarity S1 in the graph illustrated in FIG. 23 is used, for example, and assuming that a degree of similarity S1 of a new target material is determined to be 0.5 by calculation using optimized parameters, it is possible to predict that a relative permittivity of the target material becomes about 70.

In this manner, in the one embodiment of the technique disclosed herein, by determining a degree of similarity according to a characteristic, it is possible to predict a characteristic value of a target material with high accuracy according to the characteristic.

Figure 24A:
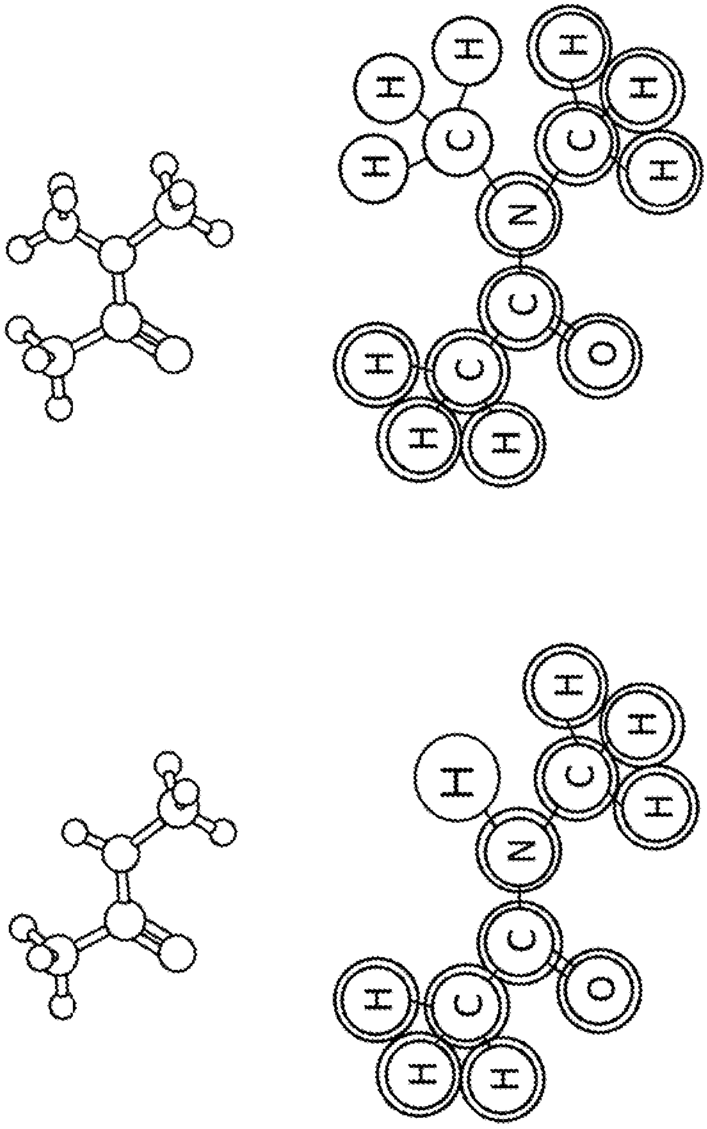
FIGS. 24A and 24B are a set of diagrams illustrating an example of a molecular structure and a graphed molecular structure, in an example in which a degree of similarity between materials having relative permittivities not close to each other is calculated to be high in the related art, and is calculated to be low in the present embodiment.
Figure 24B:
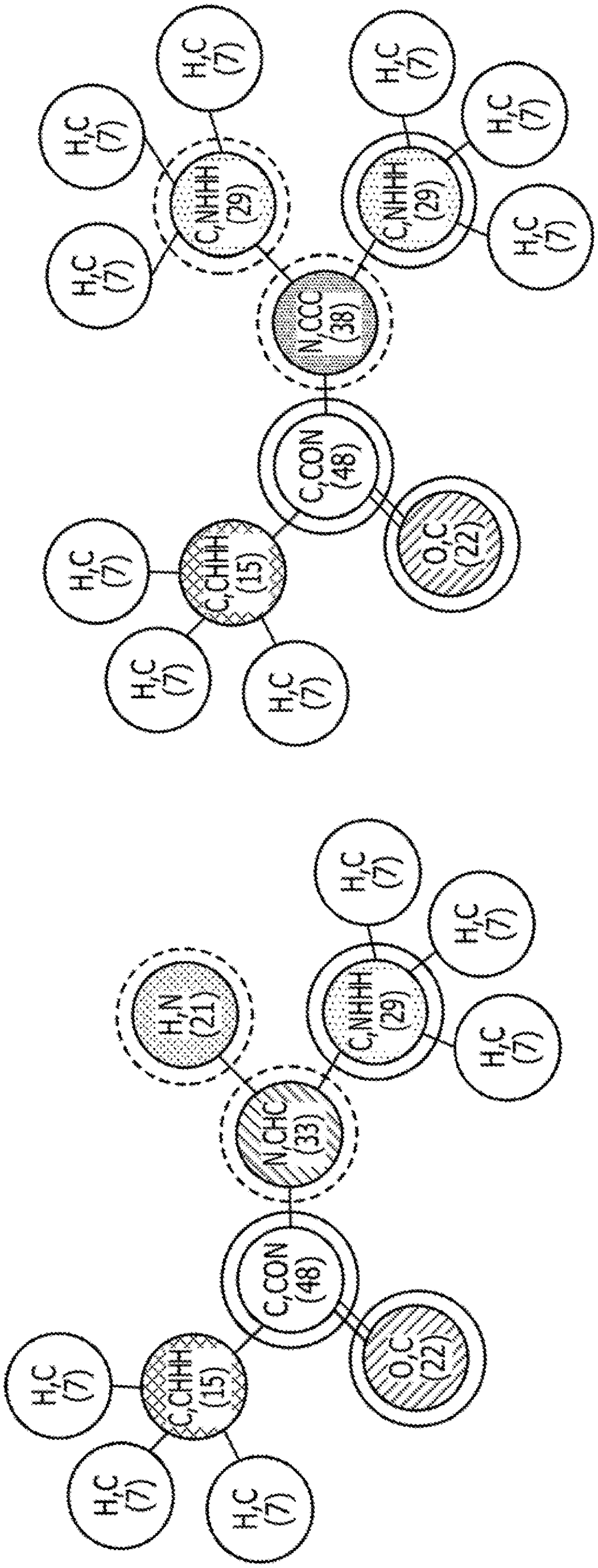

FIGS. 24A and 24B illustrate one example of a molecular structure and a graphed molecular structure, in which a degree of similarity between materials having relative permittivities not close to each other is calculated to be high in the related art of FIG. 24A, and is calculated to be low in the present embodiment FIG. 24B. In FIGS. 24A and 24B, a node atom enclosed by a circle (solid line or dotted line) is a node atom whose evaluation index $B_i$ exceeds a threshold value $B_{th}$, and a node atom enclosed by a solid circle is a node atom included in a node finally found as a maximum independent set.

In the related art of FIG. 24A, the parameters in the above formula (2) are set such that $V_C^A$=11, $V_A$=12, $V_C^B$5 =11, and $V_B$=15, and in the present embodiment, $V_C^A$=2, $V_A$=4, $V_C^B$=2, and $V_B$=3. Thus, setting δ in the formula (2) to 0.5 results in S0=0.5×(11/12+11/15)=0.825 in the related art, but S1=0.5×(3/5+3/5)=0.6 in the present embodiment.

In this manner, in the present embodiment of FIG. 24B, it is found that a degree of similarity between materials having relative permittivities not close to each other is calculated to be lower than that in the related art, and a degree of similarity according to a characteristic is calculated.

Figure 25A:
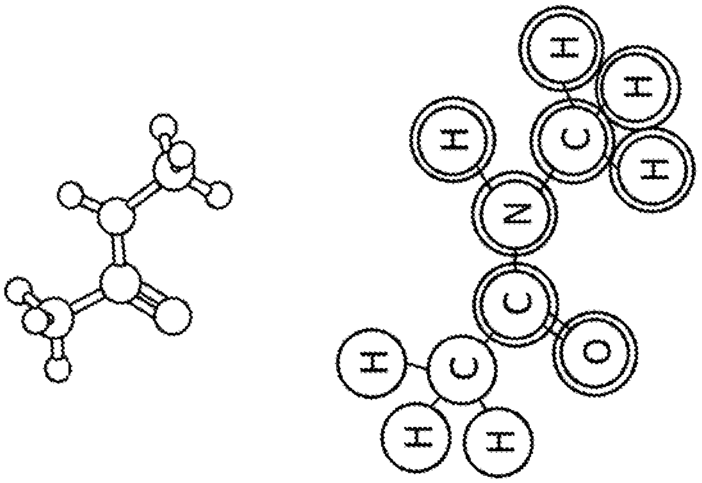
FIGS. 25A and 25B are a set of diagrams illustrating an example of a molecular structure and a graphed molecular structure, in an example in which a degree of similarity between materials having relative permittivities close to each other is calculated to be low in the related art, and is calculated to be high in the present embodiment.
Figure 25A:
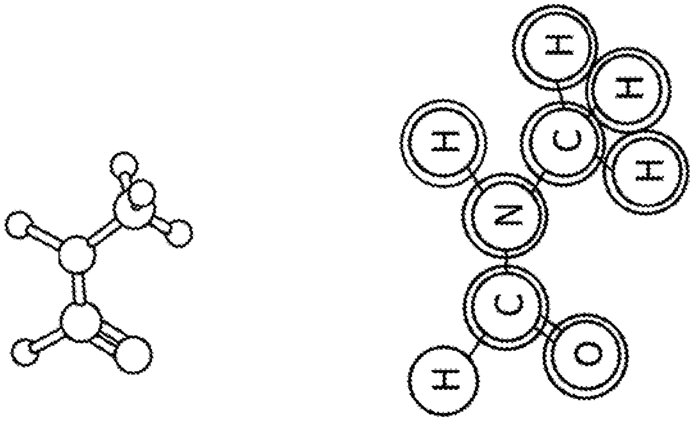
Figure 25B:
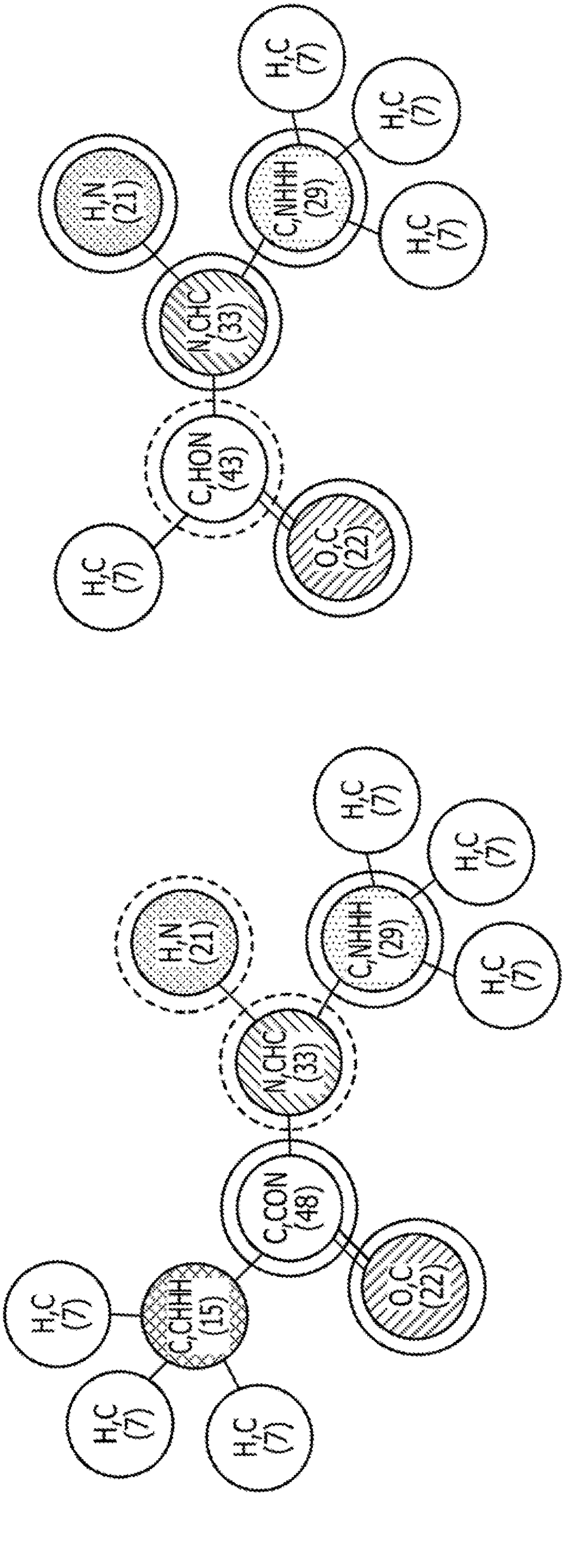

FIGS. 25A and 25B illustrate one example of a molecular structure and a graphed molecular structure, in an example in which a degree of similarity between materials having relative permittivities close to each other is calculated to be low in the related art of FIG. 25A, and is calculated to be high in the present embodiment of FIG. 25B.

In the related art, the parameters in the above formula (2) are set such that $V_C^A$=8, $V_A$=12, V=8, and $V_B$=9, and in the present embodiment, $V_C^A$=4, $V_A$=5, $V_C^B$=4, and $V_B$=5. Thus, setting δ in the formula (2) to 0.5 results in S0=0.5×(8/12+8/9)=0.7777 in the related art, but S1=0.5×(4/5+4/5)=0.8 in the present embodiment.

In this manner, in the present embodiment, it is found that a degree of similarity between materials having relative permittivities close to each other is calculated to be higher than that in the related art, and a degree of similarity according to a characteristic is calculated.

Figure 26A:
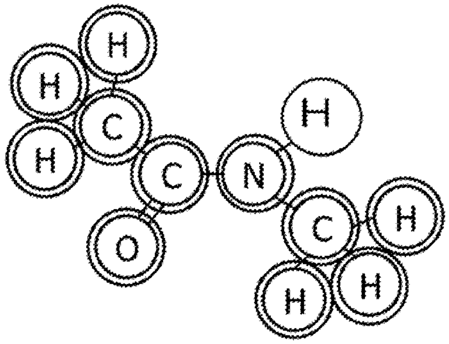
Figure 26A:
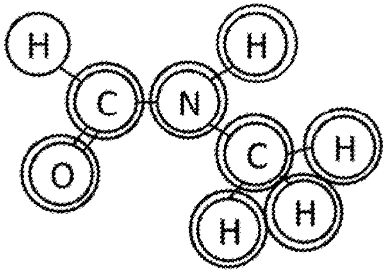
Figure 26A:
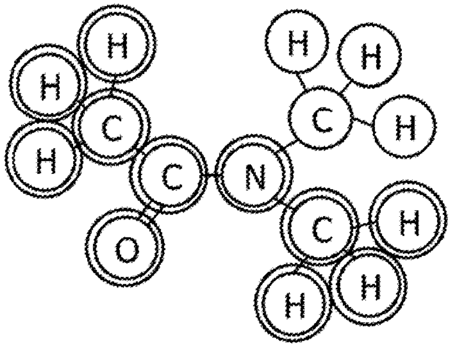
Figure 26A:
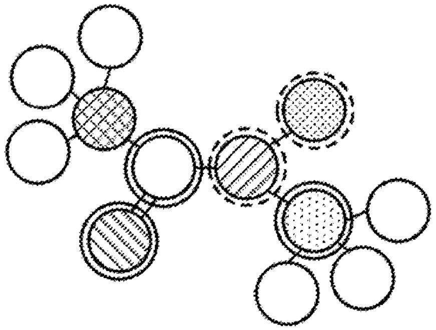
Figure 26A:
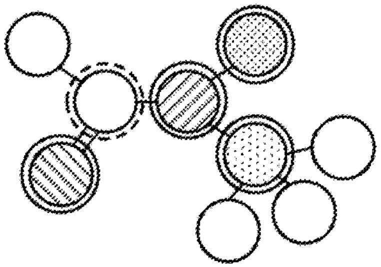
Figure 26A:
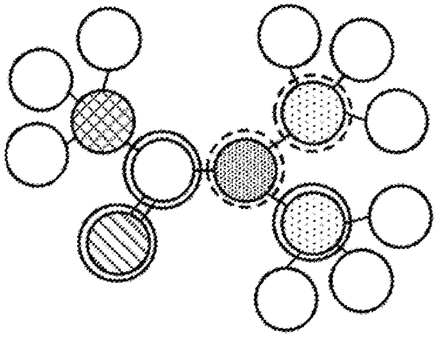

FIGS. 26A and 26B are a set of diagram illustrating one example of relationships between degree of similarity and characteristic value, in the one embodiment of the technique disclosed herein and in the related art.

As illustrated in FIGS. 26A and 26B, when N-methylacetamide is used as a query material, a degree of similarity calculated from only structure as the related art is 0.7777, for N-methylformamide having a relative permittivity of 182.4. Similarly, when N-methylacetamide is used as a query material, a degree of similarity calculated from only structure as the related art is 0.825, for N,N-dimethylacetamide having a relative permittivity of 37.78.

On the other hand, when N-methylacetamide is used as a query material, a degree of similarity according to a characteristic in one example of the technique disclosed herein is 0.8, for N-methylformamide. Similarly, when N-methylacetamide is used as a query material, a degree of similarity according to a characteristic in the one example of the technique disclosed herein is 0.6, for N,N-dimethylacetamide.

For example, as illustrated in FIGS. 26A and 26B, magnitude of a degree of similarity calculated only from structure as the related art of does not correspond to magnitude of a relative permittivity, and it is considered to be difficult to predict a relative permittivity by using this degree of similarity. On the other hand, magnitude of a degree of similarity according to a characteristic in the one example of the technique disclosed herein corresponds to magnitude of a relative permittivity, and it is possible to accurately predict a characteristic value of a characteristic of a target material.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An apparatus for predicting characteristics of a new chemical substance, comprising:

a memory; and a processor, coupled to the memory, configured to:

determine a degree of similarity between a target material and a first material based on a structure and characteristic of each of the target material and the first material;

predict a characteristic value of the target material based on a first value representing the characteristic of the first material;

output the predicted characteristic value; and predict characteristics of the new chemical substance based on the output predicted characteristic value, wherein the processor uses $$H = -\alpha\sum_{i=0}^{n-1} b_i x_i + \beta\sum_{i,j=0}^{n-1} w_{ij} x_i x_j \tag{1}$$

to search for a maximum independent set based on a molecular structure of each of the target material and the first material to determine the degree of similarity according to the characteristic, in the formula (1), the H is a hamiltonian for minimizing the H which searches for the maximum independent set, the n is a number of nodes in a conflict graph of the target material and the first material, the conflict graph is a graph created based on a rule that when a combination of each node atom of the graphed target material and each node atom of the graphed first material is defined as the node, comparing the multiple nodes of the graph;

an edge is created between the nodes that are compared and determined to not be identical, no edge is created between the nodes that are compared and determined to be identical to each other, the $b_i$ is a numerical value which represents a bias for the node ordered i-th, the $w_{ij}$ is a positive number that is not 0 when an edge exists between the i-th node and the j-th node, and is 0 when no edge exists between the i-th node and the j-th node, the $x_i$ is a binary variable indicating that the node ordered i-th is 0 or 1, the $x_j$ is a binary variable indicating that the node ordered j-th is 0 or 1, and the α and the β are positive numbers, wherein the processor uses $$S(G_A, G_B) = \delta\max\left\{\frac{|V_C^A|}{|V_A|}, \frac{|V_C^B|}{|V_B|}\right\} + (1-\delta)\min\left\{\frac{|V_C^A|}{|V_A|}, \frac{|V_C^B|}{|V_B|}\right\} \tag{2}$$

to determine the degree of similarity according to the characteristic for a found maximum independent set, in the above formula (2), the $G_A$ represents the target material graphed, the $G_B$ represents the first material graphed, the $S(G_A, G_B)$ represents a degree of similarity between the target material graphed and the first material graphed, is expressed as 0 to 1, and indicates that a degree of similarity is higher, as the $S(G_A, G_B)$ approaches 1, the $V_A$ represents a total number of node atoms in the target material graphed, the $V_C^A$ represents the number of the node atoms included in a maximum independent set of the conflict graph among the node atoms in the target material graphed, the $V_B$ represents a total number of the node atoms in the first material graphed, the $V_C^B$ represents the number of the node atoms included in a maximum independent set of the conflict graph among the node atoms in the first material graphed, and the δ is a number of 0 to 1, the processor further configured to add a WL label according to a Weisfeiler-Lehman (WL) procedure to the node atom, wherein the processor, when using the formula (1) to determine the degree of similarity according to the characteristic, selects the node atom according to an evaluation index Bi for expression of the characteristic based on information of the WL label, the processor, in order to increase a correlation coefficient determined between the degree of similarity according to the characteristic and the characteristic value according to the characteristic, updates at least one of i) a numerical value of a contribution value ΔB for each type of atom of the node atom, serving as a criterion for calculating a value of the evaluation index $B_i$ included in information of the WL label added to the node atom of the node ordered i-th, in the formula (1), ii) a threshold value of the evaluation index $B_i$ included in information of the WL label added to the node atom constituting the node ordered i-th, in the formula (1), iii) a numerical value of the $b_i$, in the formula (1), iv) a numerical value of the $w_{ij}$, in the formula (1), and v) a similarity degree evaluation formula S represented by the formula (2), wherein the update is performed according to genetic algorithm of a machine learning method.

2. The apparatus according to claim 1, wherein the processor, when a correlation coefficient determined between the degree of similarity according to the characteristic and the characteristic value according to the characteristic exceeds a threshold value, outputs the degree of similarity according to the characteristic of the target material.

3. The apparatus according to claim 1, wherein the processor, when a correlation coefficient determined between the degree of similarity according to the characteristic and the characteristic value according to the characteristic exceeds a threshold value, predicts the characteristic value in the target material.

4. The apparatus according to claim 1, wherein the memory is configured to store a chemical structure data group of a plurality of the first materials.

5. The apparatus according to claim 1, wherein the memory is configured to store a chemical structure data group of a plurality of the target materials.

6. The apparatus according to claim 1, the processor is further configured to add the WL label to the node atom, and in one node in the node atoms, derive the WL label from information of the one node atom, and information on a bonded node atom to which the one node atom is bonded.

7. The apparatus according to claim 1, wherein the evaluation index $B_i$ means a sum of a contribution value ΔB to an expression of the characteristic calculated for each type of atom of the node atom within each of the target material and the first material.

8. The apparatus according to claim 1, wherein the processor, when using the formula (1) to determine the degree of similarity according to the characteristic, sets the $b_i$ in the formula (1)

to a numerical value corresponding to magnitude of the evaluation index B, included in information of the WL label added to the node atom of the node ordered i-th.

9. The apparatus according to claim 1, wherein the processor, when using the formula (1) to determine the degree of similarity according to the characteristic, sets the $b_i$ in the formula (1)

to a positive number, when the evaluation index B, included in information of the WL label added to the node atom of the node ordered i-th exceeds a threshold value, and to a negative number, when the evaluation index B included in information of the WL label added to the node atom of the node ordered i-th is equal to or less than a threshold value.

10. The apparatus according to claim 1, wherein the processor minimizes a hamiltonian (H) in the formula (1) according to an annealing method to search for the maximum independent set.

11. A method for causing a processor to execute a process for predicting characteristics of a new chemical substance, the process comprising:

determining a degree of similarity between a target material and a first material based on a structure and characteristic of each of the target material and the first material;

predicting a characteristic value of the target material based on a first value representing the characteristic of the first material;

outputting the predicted characteristic value; and predicting characteristics of the new chemical substance based on the output predicted characteristic value, wherein the process uses $$H = -\alpha\sum_{i=0}^{n-1} b_i x_i + \beta\sum_{i,j=0}^{n-1} w_{ij} x_i x_j \quad (1)$$

to search for a maximum independent set based on a molecular structure of each of the target material and the first material to determine the degree of similarity according to the characteristic, in the formula (1), the H is a hamiltonian for minimizing the H which searches for the maximum independent set, the n is a number of nodes in a conflict graph of the target material and the first material, the conflict graph is a graph created based on a rule that when a combination of each node atom of the graphed target material and each node atom of the graphed first material is defined as the node, comparing the multiple nodes of the graph;

an edge is created between the nodes that are compared and determined to not be identical, no edge is created between the nodes that are compared and determined to be identical to each other, the $b_i$ is a numerical value which represents a bias for the node ordered i-th, the $w_{ij}$ is a positive number that is not 0 when an edge exists between the i-th node and the j-th node, and is 0 when no edge exists between the i-th node and the j-th node, the $x_i$ is a binary variable indicating that the node ordered i-th is 0 or 1, the $x_j$ is a binary variable indicating that the node ordered j-th is 0 or 1, and the α and the β are positive numbers, wherein the process uses $$S(G_A, G_B) = \delta\max\left\{\frac{|V_C^A|}{|V_A|}, \frac{|V_C^B|}{|V_B|}\right\} + (1-\delta)\min\left\{\frac{|V_C^A|}{|V_A|}, \frac{|V_C^B|}{|V_B|}\right\} \quad (2)$$

to determine the degree of similarity according to the characteristic for a found maximum independent set, in the above formula (2), the $G_A$ represents the target material graphed, the $G_B$ represents the first material graphed, the $S(G_A, G_B)$ represents a degree of similarity between the target material graphed and the first material graphed, is expressed as 0 to 1, and indicates that a degree of similarity is higher, as the $S(G_A, G_B)$ approaches 1, the $V_A$ represents a total number of node atoms in the target material graphed, the $V_C{}^A$ represents the number of the node atoms included in a maximum independent set of the conflict graph among the node atoms in the target material graphed, the $V_B$ represents a total number of the node atoms in the first material graphed, the $V_C{}^B$ represents the number of the node atoms included in a maximum independent set of the conflict graph among the node atoms in the first material graphed, and the δ is a number of 0 to 1, the process adds a WL label according to a Weisfeiler-Lehman (WL) procedure to the node atom, wherein the process, when using the formula (1) to determine the degree of similarity according to the characteristic, selects the node atom according to an evaluation index Bi for expression of the characteristic based on information of the WL label, the process, in order to increase a correlation coefficient determined between the degree of similarity according to the characteristic and the characteristic value according to the characteristic, updates at least one of i) a numerical value of a contribution value ΔB for each type of atom of the node atom, serving as a criterion for calculating a value of the evaluation index B, included in information of the WL label added to the node atom of the node ordered i-th, in the formula (1), ii) a threshold value of the evaluation index B included in information of the WL label added to the node atom constituting the node ordered i-th, in the formula (1), iii) a numerical value of the $b_i$, in the formula (1), iv) a numerical value of the $w_{ij}$, in the formula (1), and v) a similarity degree evaluation formula S represented by the formula (2), wherein the update is performed according to genetic algorithm of a machine learning method.

12. A non-transitory computer-readable recording medium having stored therein a program for causing a processor to execute a process for predicting characteristics of a new chemical substance, the process comprising:

determining a degree of similarity between a target material and a first material based on a structure and characteristic of each of the target material and the first material;

predicting a characteristic value of the target material based on a first value representing the characteristic of the first material;

outputting the predicted characteristic value; and predicting characteristics of the new chemical substance based on the output predicted characteristic value, wherein the process uses $$H = -\alpha\sum_{i=0}^{n-1} b_i x_i + \beta\sum_{i,j=0}^{n-1} w_{ij} x_i x_j \quad (1)$$

to search for a maximum independent set based on a molecular structure of each of the target material and the first material to determine the degree of similarity according to the characteristic, in the formula (1), the H is a hamiltonian for minimizing the H which searches for the maximum independent set, the n is a number of nodes in a conflict graph of the target material and the first material, the conflict graph is a graph created based on a rule that when a combination of each node atom of the graphed target material and each node atom of the graphed first material is defined as the node, comparing the multiple nodes of the graph;

an edge is created between the nodes that are compared and determined to not be identical, no edge is created between the nodes that are compared and determined to be identical to each other, the $b_i$ is a numerical value which represents a bias for the node ordered i-th, the $w_{ij}$ is a positive number that is not 0 when an edge exists between the i-th node and the j-th node, and is 0 when no edge exists between the i-th node and the j-th node, the $x_i$ is a binary variable indicating that the node ordered i-th is 0 or 1, the $x_j$ is a binary variable indicating that the node ordered j-th is 0 or 1, and the $\alpha$ and the $\beta$ are positive numbers, wherein the process uses $$S(G_A, G_B) = \delta\max\left\{\frac{|V_C^A|}{|V_A|}, \frac{|V_C^B|}{|V_B|}\right\} + (1-\delta)\min\left\{\frac{|V_C^A|}{|V_A|}, \frac{|V_C^B|}{|V_B|}\right\} \quad (2)$$

to determine the degree of similarity according to the characteristic for a found maximum independent set, in the above formula (2), the $G_A$ represents the target material graphed, the $G_B$ represents the first material graphed, the $S(G_A, G_B)$ represents a degree of similarity between the target material graphed and the first material graphed, is expressed as 0 to 1, and indicates that a degree of similarity is higher, as the $S(G_A, G_B)$ approaches 1, the $V_A$ represents a total number of node atoms in the target material graphed, the $V_C{}^A$ represents the number of the node atoms included in a maximum independent set of the conflict graph among the node atoms in the target material graphed, the $V_B$ represents a total number of the node atoms in the first material graphed, the $V_C{}^B$ represents the number of the node atoms included in a maximum independent set of the conflict graph among the node atoms in the first material graphed, and the $\delta$ is a number of 0 to 1, the process adds a WL label according to a Weisfeiler-Lehman (WL) procedure to the node atom, wherein the process, when using the formula (1) to determine the degree of similarity according to the characteristic, selects the node atom according to an evaluation index Bi for expression of the characteristic based on information of the WL label, the process, in order to increase a correlation coefficient determined between the degree of similarity according to the characteristic and the characteristic value according to the characteristic, updates at least one of i) a numerical value of a contribution value $\Delta B$ for each type of atom of the node atom, serving as a criterion for calculating a value of the evaluation index B, included in information of the WL label added to the node atom of the node ordered i-th, in the formula (1), ii) a threshold value of the evaluation index B included in information of the WL label added to the node atom constituting the node ordered i-th, in the formula (1), iii) a numerical value of the $b_i$, in the formula (1), iv) a numerical value of the $w_{ij}$, in the formula (1), and v) a similarity degree evaluation formula S represented by the formula (2), wherein the update is performed according to genetic algorithm of a machine learning method.

* * * * *